United States Patent [19]

Terada et al.

[11] Patent Number: 5,756,730
[45] Date of Patent: May 26, 1998

[54] PROCESS FOR PREPARING ANALGESIC COMPOUNDS

[75] Inventors: Atsusuke Terada; Yoshio Iizuka; Kazuyuki Wachi; Kenji Fujibayashi, all of Tokyo, Japan

[73] Assignee: Sankyo Company, Limited, Tokyo, Japan

[21] Appl. No.: 789,941

[22] Filed: Jan. 28, 1997

Related U.S. Application Data

[62] Division of Ser. No. 409,865, Mar. 24, 1995, Pat. No. 5,656,758, which is a division of Ser. No. 373,469, Jan. 17, 1995, Pat. No. 5,512,567, which is a continuation of Ser. No. 140,602, Oct. 21, 1993, abandoned, which is a division of Ser. No. 943,386, Sep. 10, 1992, Pat. No. 5,270,327, which is a continuation of Ser. No. 627,736, Dec. 14, 1990, abandoned, which is a division of Ser. No. 397,105, Aug. 22, 1989, Pat. No. 5,021,413.

[30] Foreign Application Priority Data

Aug. 24, 1988 [JP] Japan ................................ 1-210074

[51] Int. Cl.$^6$ .................... C07D 403/14; C07D 402/14
[52] U.S. Cl. .................... 544/60; 544/124; 544/242; 544/360; 546/186; 546/187; 546/226; 546/207; 546/214
[58] Field of Search ............................ 544/60, 124, 242, 544/360; 546/186, 187, 226, 207–214

[56] References Cited

U.S. PATENT DOCUMENTS

| | | | |
|---|---|---|---|
| Re. 33,906 | 4/1992 | Vecchietti et al. | 514/210 |
| 3,917,617 | 11/1975 | Razdan et al. | 544/130 |
| 4,304,911 | 12/1981 | Zenitz | 544/130 |
| 4,339,576 | 7/1982 | Zenitz | 544/130 |
| 4,396,765 | 8/1993 | Zenitz | 544/129 |
| 4,774,241 | 9/1988 | Tatsuoka et al. | 544/130 |
| 4,801,585 | 1/1989 | Vecchietti et al. | 514/210 |
| 4,826,819 | 5/1989 | Vecchietti et al. | 514/212 |
| 4,879,300 | 11/1989 | Giordani et al. | 514/210 |
| 4,923,863 | 5/1990 | Scopes et al. | 514/210 |
| 4,943,578 | 7/1990 | Naylor et al. | 514/210 |
| 4,994,450 | 2/1991 | Vecchietti et al. | 514/183 |
| 5,087,630 | 2/1992 | Colle et al. | 514/307 |
| 5,089,507 | 2/1992 | Vecchietti et al. | 514/326 |
| 5,116,842 | 5/1992 | Naylor et al. | 514/210 |

FOREIGN PATENT DOCUMENTS

| | | | |
|---|---|---|---|
| 0 232 612 | 8/1987 | European Pat. Off. | |
| 323612 | 8/1987 | European Pat. Off. | 514/210 |
| 0 260 041 | 3/1988 | European Pat. Off. | |

OTHER PUBLICATIONS

Chemical Abstracts, Wu et al. "Phenylalanyl perhydro thiazine . . . " CA 110: 24292n, p. 24301 (1989).
Chemical Abstracts, Wu et al. "Phenylalanyl perhydro thiazine . . . " CA 110: 24293p, p. 24301 (1989).
Chemical Abstracts, Blaschke et al. "Preparation, optical purity and configuration of the enantiomers of flecainide" vol. 104, No. 11, Mar. 17, 1986, p. 644, Abstract No. 88 404j of Chem. Ber. (1985), 118(11), 4616–4619.
Blaschke et al. "Herstellung, optische Reinheit und Konfiguration der Flecainid–Enantiomeren", Chem. Ber. 118(11), 4616–4619 (1985).
Chemical Abstracts, CA108(7): 55897b (1987) of EP 232612, Aug. 1987.
Scopes, "Recent developments in non–peptide kappa receptor agonists", (1993) 18, 933–947, *Drugs of the Future*.
Giardina et al. "Overview", Selective, Non–peptidic kappa–opioid Agonists, *Current Opinion in Therapeutic Patents*, (1991), vol. 1, No. 3, 345–362.
O'Brien, "Receptor Binding Drug Research", (1987), Marcel Dekker, Inc. pp. 185–187, 192.

*Primary Examiner*—Matthew V. Grumbling
*Attorney, Agent, or Firm*—Frishauf, Holtz, Goodman, Langer & Chick, P.C.

[57] ABSTRACT

A process for preparing a compound of the formula (I)

$$E\underset{CH_2NR^1R^2}{\overset{}{\diagdown}}N-\overset{O}{\overset{\|}{C}}-\overset{R^3}{\overset{|}{CH}}-\overset{R^4}{\overset{|}{C}}\underset{A}{\diagup}C \quad (I)$$

in which, $R^1$ and $R^2$ are the same or different and each is hydrogen or $C_1$–$C_6$ alkyl, or $R^1$ and $R^2$ together with the nitrogen atom to which they are attached form a heterocyclic ring which is unsubstituted or substituted and is a 5-membered or 6-membered N-heterocycle which optionally has a further heteroatom which is oxygen, nitrogen or sulfur; E is methylene; ring A is a unsubstituted or unsubstituted aryl ring, or a substituted or an unsubstituted heteroaryl ring; $R^3$ is a $C_1$–$C_6$ alkyl and $R^4$ is hydrogen, or $R^3$ and $R^4$ together are a group of the formula —(CR$^a$R$^b$)$_m$— C(=Y)— (IV), wherein each of $R^a$ and $R^b$ is hydrogen or $C_1$–$C_3$ alkyl, provided that there are not more than three alkyl groups in the formula (IV), m is 1, 2, or 3, and Y is two hydrogens or an oxygen; or a pharmaceutically acceptable salt thereof; which process comprises reacting an acid of the formula (II)

$$\overset{R^4}{\overset{|}{C}}\underset{A}{\diagdown}\overset{R^3}{\overset{|}{C}}-CH-\overset{O}{\overset{\|}{C}}-OH \quad (II)$$

with an amine of the following formula (III)

$$E\underset{CH_2NR^1R^2}{\overset{}{\diagdown}}N-H \quad (III)$$

15 Claims, No Drawings

PROCESS FOR PREPARING ANALGESIC COMPOUNDS

This application is a division of application Ser. No. 08/409,865 filed Mar. 24, 1995, (now U.S. Pat. No. 5,656, 758) which is a division of application Ser. No. 08/373,469 filed Jan. 17, 1995, (now U.S. Pat. No. 5,512,567) which is a continuation of application Ser. No. 08/140,602 filed Oct. 21, 1993 (abandoned), which is a division of application Ser. No. 07/943,386 filed Sep. 10, 1992 (now U.S. Pat. No. 5,270,327), which is a continuation of application Ser. No. 07/627,736 filed Dec. 14, 1990 (abandoned), which is a division of application Ser. No. 07/397,105 filed Aug. 22, 1989 (now U.S. Pat. No. 5,021,413).

BACKGROUND OF THE INVENTION

The present invention relates to carboxylic acid amide derivatives and pharmaceutically acceptable acid addition salts thereof, being compounds which have useful analgesic and other pharmaceutical activity, and further relates to the preparation of such compounds.

In general, analgesic drugs acting on κ-receptors do not show the side effects such as dependence, drug tolerance and respiratory inhibition shown by the morphine-like analgesic drugs acting on μ-receptors. Furthermore, analgesic drugs acting on κ-receptors do not show cross resistance to morphine. Accordingly, the analgesic drugs acting on κ-receptors are of considerable interest, because an agent which does not evince respiratory inhibition is useful for management of post-operative patients suffering from pain. Moreover, an agent without cross resistance is significant in clinical uses, for example, for patients suffering from cancer pain where tolerance to morphine and other antagonistic analgesic agents has occurred.

By way of example, European Patent Specification 232612 published on 19 Aug. 1987 discloses azacyclic compounds which exhibit K-receptor agonism. The compounds are without the behavioural effects of morphine and morphine analogs, and are thus of potential therapeutic utility as analgesics. A small class of compounds within the generality of European Patent Specification 232612 and said to have improved properties are disclosed in European Patent Specification 260041 published on 16 Mar. 1988.

OBJECTS OF THE PRESENT INVENTION

The objects of the present invention include compounds which have pharmacological activity and in particular are useful as analgesic agents. Further objects comprise pharmaceutical compositions with analgesic or other pharmacological activity, as well as methods for the relief of pain using the compounds and processes for the preparation of such compounds.

SUMMARY OF THE PRESENT INVENTION

The present invention provides compounds of the general formula (I):

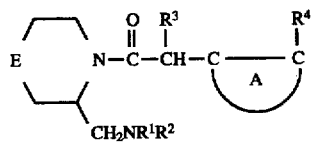

in which, $R^1$ and $R^2$ are the same or different and each represents a hydrogen atom or a $C_1$–$C_6$ alkyl group, or $R^1$ and $R^2$ together with the nitrogen atom to which they are attached form a heterocyclic ring;

E represents a methylene group, a sulfur atom, an oxygen atom or an imino group optionally substituted with a $C_1$–$C_6$ alkyl group or an aralkyl group;

the ring A represents an aryl ring; a heteroaryl ring; an aryl ring substituted with at least one substituent selected from Group (i); or a heteroaryl ring substituted with at least one substituent selected from Group (i);

said Group (i) comprising halogen atoms, $C_1$–$C_6$ alkyl groups, halogenated $C_1$–$C_6$ alkyl groups, $C_1$–$C_6$ alkoxy groups, halogenated $C_1$–$C_6$ alkoxy groups, $C_1$–$C_6$ alkylthio groups, aryl groups, acyl groups, nitro groups, and hydroxy groups;

$R^3$ represents a hydrogen atom or a $C_1$–$C_6$ alkyl group and $R^4$ represents a hydrogen atom, or $R^3$ and $R^4$ together represent a group of formula (IV):

$$—(CR^aR^b)_m—C(=Y)—\qquad\text{(IV)}$$

(wherein each $R^a$ and $R^b$ represents hydrogen or a $C_1$–$C_3$ alkyl group, provided that there are not more than three alkyl groups in the group of formula (IV), m represents 1, 2, or 3, and Y represents two hydrogen atoms or an oxygen atom);

provided that when E represents a methylene group, then $R^3$ is a $C_1$–$C_6$ alkyl group or $R^3$ and $R^4$ together represent a group of the formula (IV);

and pharmaceutically acceptable salts thereof.

Compounds wherein E represents a methylene group, and $R^3$ and $R^4$ both represent hydrogen atoms are excluded in view of the disclosure in European Patent Specification 232612, mentioned above.

The present invention thus embraces compounds of general formula (I) and salts thereof, wherein $R^3$ is a $C_1$–$C_6$ alkyl group and R is a hydrogen atom, or $R^3$ and $R^4$ together represent said group of formula (IV); and further embraces compounds of formula (I) wherein E is selected from the group consisting of a sulfur atom, an oxygen atom, an imino group, and imino groups substituted with a substituent selected from the group consisting of $C_1$–$C_6$ alkyl groups and aralkyl groups; and $R^3$ and $R^4$ both represent hydrogen atoms.

PREFERRED EMBODIMENTS OF THE PRESENT INVENTION

Preferred embodiments include those compounds wherein $R^1$ and $R^2$ are the same or different and each is a $C_1$–$C_6$ alkyl group, or $R^1$ and $R^2$ together with the nitrogen atom to which they are attached form a 5- or 6-membered heterocyclic ring;

E is selected from the group consisting of a methylene group, a sulfur atom and an imino group;

ring A is selected from the group consisting of aryl rings; heteroaryl rings; aryl rings substituted with at least one substituent of Group (ii); and heteroaryl rings substituted with at least one substituent of Group (ii);

said Group (ii) being a subset of Group (i) and comprising halogen atoms, halogenated $C_1$–$C_6$ alkyl groups, and $C_1$–$C_6$ alkyl groups;

$R^3$ and $R^4$ both represent hydrogen atoms, or $R^3$ and $R^4$ together represent a group of formula (IV):

$$—(CR^aR^b)_m—C(=Y)—\qquad\text{(IV)}$$

(wherein each $R^a$ and $R^b$ represents hydrogen or a $C_1$–$C_3$ alkyl group, provided that there is not more than one alkyl group in the group of formula (IV), m represents 1, or 2, and Y represents two hydrogen atoms or an oxygen atom); and pharmaceutically acceptable salts thereof.

More preferred embodiments include those compounds wherein $R^1$ and $R^2$ are the same or different and each is a $C_1$-$C_3$ alkyl group, or $R^1$ and $R^2$ together with the nitrogen atom to which they are attached form a pyrrolidine ring or a piperidine ring;

E is selected from the group consisting of a methylene group and a sulfur atom;

ring A is selected from the group consisting of aryl rings; heteroaryl rings; and aryl rings substituted with at least one substituent selected from the group consisting of halogen atoms, halogenated $C_1$-$C_3$ alkyl groups, and $C_1$-$C_3$ alkyl groups;

$R^3$ and $R^4$ both represent hydrogen atoms, or $R^3$ and $R^4$ together represent a group of formula (IV):

 (IV)

(wherein each $R^a$ and $R^b$ represents a hydrogen atom, m represents 1, or 2, and Y represents two hydrogen atoms or an oxygen atom);

and pharmaceutically acceptable salts thereof.

Most preferred embodiments include those compounds wherein $R^1$ and $R^2$ together with the nitrogen atom to which they are attached form a pyrrolidine ring or a piperidine ring:

E is selected from the group consisting of a methylene group and a sulfur atom;

ring A is selected from the group consisting of aryl rings and aryl rings substituted with at least one substituent selected from the group consisting of halogen atoms and $C_1$-$C_3$ alkyl groups;

$R^3$ and $R^4$ together represent a group of formula (IV):

 (IV)

(wherein each $R^a$ and $R^b$ represents hydrogen atom, m represents 1, or 2, and Y represents two hydrogen atoms or an oxygen atom);

and pharmaceutically acceptable salts thereof.

Further embodiments include:

compounds wherein $R^1$ and $R^2$ together with the nitrogen atom to which they are attached form a pyrrolidine ring or a piperidine ring;

E is selected from the group consisting of a methylene group and a sulfur atom;

ring A is an aryl ring substituted with at least one substituent selected from the group consisting of halogen atoms and $C_1$-$C_3$ alkyl groups;

$R^3$ and $R^4$ together represent a group of formula (IV):

 (IV)

(wherein each $R^a$ and $R^b$ represents a hydrogen atom, m represents 1, or 2, and Y represents two hydrogen atoms or an oxygen atom);

compounds wherein $R^1$ and $R^2$ both represent $C_1$-$C_3$ alkyl groups;

E is selected from the group consisting of a methylene group and a sulfur atom;

ring A is selected from the group consisting of aryl rings; aryl rings substituted with at least one substituent selected from the group comprising halogen atoms and $C_1$-$C_3$ alkyl groups;

$R^3$ and $R^4$ together represent a group of formula (IV):

 (IV)

(wherein each $R^a$ and $R^b$ represents a hydrogen atom, m represents 1 or 2, and Y represents two hydrogen atoms or an oxygen atom);

compounds wherein $R^1$ and $R^2$ both represent $C_1$-$C_3$ alkyl groups;

E is selected from the group consisting of a methylene group and a sulfur atom;

ring A is an aryl ring substituted with at least one substituent selected from the group consisting of halogen atoms and $C_1$-$C_3$ alkyl groups;

$R^3$ and $R^4$ together represent a group of formula (IV):

 (IV)

(wherein each $R^a$ and $R^b$ represents a hydrogen atom, m represents 1 or 2, and Y represents two hydrogen atoms or an oxygen atom);

compounds wherein $R^1$ and $R^2$ together with the nitrogen atom to which they are attached form a pyrrolidine ring or a piperidine ring;

compounds wherein E is selected from the group consisting of a methylene group and a sulfur atom;

compounds wherein ring A is selected from the group consisting of aryl rings and aryl rings substituted with at least one substituent selected from the group consisting of halogen atoms and $C_1$-$C_3$ alkyl groups: and compounds wherein $R^3$ and $R^4$ together represent a group of formula (IV):

 (IV)

(wherein each $R^a$ and $R^b$ represents a hydrogen atom, m represents 1, or 2, and Y represents two hydrogen atoms or an oxygen atom);

and pharmaceutically acceptable salts thereof.

In the general formula (I), the groups $R^1$ and $R^2$ are the same or different and each represents a hydrogen atom, or a straight or branched chain $C_1$-$C_6$ alkyl group preferably having from 1 to 3 carbon atoms. Examples of suitable alkyl groups include a methyl, ethyl, propyl, isopropyl, butyl, isobutyl, s-butyl, t-butyl, pentyl, isopentyl, 2-methylbutyl, t-pentyl, neopentyl, hexyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 2,3-dimethylbutyl, or 1,3-dimethylbutyl group. Of these, a methyl, ethyl, propyl, or isopropyl group is preferred.

Alternatively, $R^1$ and $R^2$ together with the nitrogen atom to which they are attached form a heterocyclic ring, preferably a saturated heterocyclic ring, and more preferably a 5- or 6-membered N-heterocycle optionally having a further heteroatom which may be oxygen, nitrogen or sulfur. Examples of suitable heterocyclic radicals represented by such rings include an imidazolidinyl, hexahydropyridazinyl, hexahydropyrimidinyl, piperazinyl, hexamethyleneimino, 1,2-diazacycloheptyl, 1,3-diazacycloheptyl, homopiperazinyl, pyrrolyl, azepinyl, thiazolidinyl, morpholinyl, thiomorpholinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, pyrazinyl, quinolyl, isoquinolyl, acridyl, tetrahydroacridyl, pyrrolidinyl, piperidino, tetrahydroquinolyl, tetrahydroisoquinolyl, isoindolyl, indolinyl or 6-azabicyclo[3.2.1]oct-6-yl group. The heterocyclic ring may be substituted with a straight or branched chain $C_1$–$C_6$ alkyl group, preferably an alkyl group having 1 to 3 carbon atoms. For example, a 6-azabicyclo[3.2.1]oct-6-yl ring may be 1,3,3-trimethyl substituted, and a piperazine ring may be N-substituted for instance with a straight or branched chain $C_1$–$C_6$ alkyl group, preferably an alkyl group having 1 to 3 carbon atoms, such as a methyl, ethyl, propyl or isopropyl group. Preferred heterocyclic rings which may be formed by $R^1$ and $R^1$ comprise a pyrrolidine, piperidine, N-methylpiperazine, morpholine, hexamethyleneimino or thiazolidine ring.

Particularly preferred examples for the group formed by $R^1$ and $R^2$ together with the nitrogen to which they are attached include monoalkyl- and dialkyl-substituted amino groups in which the or each alkyl group contains from 1 to 6, preferably from 1 to 3, carbon atoms such as a methylamino, ethylamino, propylamino, isopropylamino, butylamino, isobutylamino, dimethylamino, diethylamino, dipropylamino, diisopropylamino, pentylamino or hexylamino group, of which a methylamino, dimethylamino, ethylamino, propylamino, or isopropylamino group is preferred. The particularly preferred examples for the group formed by $R^1$ and $R^2$ together with the nitrogen to which they are attached further include a heterocyclic radical such as a 1-pyrrolidinyl, 1-piperidyl (that is, piperidino), 1-(4-methyl)piperazinyl, 1-hexamethyleneiminyl, 3-thiazolidinyl, or 4-morpholinyl (that is, morpholino) group.

The symbol E represents a methylene group, a sulfur atom, an oxygen atom or an imino group. The imino group can be substituted with a $C_1$–$C_6$ alkyl group or with an aralkyl group having 1 to 4 carbon atoms in the alkyl part and 6 or 10 carbon atoms in the aryl part. Examples of such substitutent groups for an imino group include a benzyl, phenethyl, 1-phenylethyl, 1-phenylpropyl, 2-phenylpropyl, 3-phenylpropyl, 4-phenylbutyl, 1-naphthylmethyl or 2-naphthylmethyl groups, more preferably a $C_7$–$C_9$ aralkyl group such as a benzyl group.

The ring A is preferably an aromatic ring such as an aryl ring, for instance a benzene or naphthalene ring, or a 5- to 7-membered heteroaryl ring containing 1 to 3 oxygen heteroatoms, nitrogen heteroatoms and/or sulfur heteroatoms, optionally condensed with a further ring. Heteroaryl examples for the ring A include a furan, thiophene, pyrazole, imidazole, oxazole, isoxazole, thiazole, isothiazole, triazole, thiadiazole, pyridine, pyridazine, pyrimidine, pyrazine, quinoline, isoquinoline, or acridine ring. Preferably the ring A is a benzene ring or a 5- or 6-membered heteroaryl ring containing 1 heteroatom, such as a thiophene, furan or pyridine ring.

The ring A may be substituted by one or more substituents, preferably 1 to 3 substituents, and typically 1 or 2 substituents, the substituents being of the Group (i). Such substituents may be halogen atoms such as a fluorine, chlorine, bromine and/or iodine atom; straight or branched chain $C_1$–$C_6$ alkyl groups, typically those mentioned for $R^1$ or $R^2$, and preferably straight or branched chain alkyl groups having 1 to 3 carbon atoms such as a methyl, ethyl, n-propyl or isopropyl group; aryl groups, preferably a $C_6$ or $C_{10}$ aryl group, that is a phenyl or naphthyl group; acyl groups, typically carboxylic acyl groups, preferably aliphatic acyl groups containing from 1 to 6, more preferably 1 to 4, carbon atoms such as a formyl, acetyl, propionyl, butyryl, isobutyryl, valeryl, isovaleryl, pivaloyl or hexanoyl group, of which a formyl, acetyl, propionyl, butyryl or isobutyryl group is especially preferred; straight or branched chain $C_1$–$C_6$ alkoxy groups, preferably having 1 to 3 carbon atoms, such as a methoxy, ethoxy, propoxy, isopropoxy, butoxy, isobutoxy, pentyloxy, isopentyloxy, t-pentyloxy or hexyloxy group; nitro groups: halogenated $C_1$–$C_6$ alkyl or alkoxy groups, preferably $C_1$–$C_3$ alkyl or alkoxy groups such as a fluoromethyl, difluoromethyl, trifluoromethyl, 1-fluoroethyl, 2-fluoroethyl, 2,2-difluoroethyl, 2,2,2-trifluoroethyl, 3-fluoropropyl, 4-fluorobutyl, 5-fluoropentyl, 6-fluorohexyl, 3,3-difluoropropyl, 3,3,3-trifluoropropyl, 4,4-difluorobutyl, 4,4,4-trifluorobutyl, bromomethyl, dibromomethyl, trichloromethyl, 1-chloroethyl, 2-bromoethyl, 2,2-dibromoethyl, 2,2,2-trichloroethyl, fluoromethoxy, difluoromethoxy, trifluoromethoxy, 1-fluoroethoxy, 2-fluoroethoxy, 2,2-difluoroethoxy, 2,2,2-trifluoroethoxy, 3-fluoropropoxy, 4-fluorobutoxy, 5-fluoropentyloxy, 6-fluorohexyloxy, 3,3-difluoropropoxy, 3,3,3-trifluoropropoxy, 4,4-difluorobutoxy or 4,4,4-trifluorobutoxy group, of which a fluoromethyl, difluoromethyl, trifluoromethyl, 1-fluoroethyl, 2-fluoroethyl, 2,2-difluoroethyl or 2,2,2-trifluoroethyl group is especially preferred; hydroxy groups; or straight or branched chain $C_1$–$C_6$ alkylthio groups, preferably straight or branched chain alkylthio groups having 1 to 3 carbon atoms, such as a methylthio, ethylthio, n-propylthio, isopropylthio, butylthio, isobutylthio, s-butylthio, t-butylthio, pentylthio, isopentylthio, 2-methylbutylthio, t-pentylthio, neo-pentylthio, hexylthio, 4-methylpentylthio, 3-methylpentylthio, 2-methylpentylthio, 3,3-dimethylbutylthio, 2,2-dimethylbutylthio, 1,1-dimethylbutylthio, 1,2-dimethylbutylthio, 2,3-dimethylbutylthio, or 1,3-dimethylbutylthio group.

Typical examples for the ring A include an aryl ring which is not substituted, such as, for example, a benzene or naphthalene ring; an aryl ring which is substituted with an alkyl group such as, for example, a 4-methylbenzene, 2-methylbenzene, 3-methylbenzene, 4-ethylbenzene, 4-butylbenzene, 2-propylbenzene, 3-hexylbenzene, 2,3-dimethylbenzene, 3,4-dimethylbenzene, 2,5-dimethylbenzene, 2,6-dimethylbenzene, 2,4-dimethylbenzene, 2,3-diethylbenzene, 3,4-dipropylbenzene, 2,5-dibutylbenzene, 2,6-dipentylbenzene, 2,4-dihexylbenzene, 2,3,6-trimethylbenzene, 2,3,4-trimethylbenzene, 3,4,5-trimethylbenzene, 2,5,6-trimethylbenzene, 2,4,6-trimethylbenzene, 2,3,6-triethylbenzene, 2,3,4-tripropylbenzene, 3,4,5-tributylbenzene, 2,5,6-tripentylbenzene, 2,4,6-trihexylbenzene, 1-methyl-2-naphthalene, 2-methyl-1-naphthalene, 3-methyl-1-naphthalene, 2-ethyl-1-naphthalene, 1-butyl-2-naphthalene, 2-propyl-1-naphthalene, 3-hexyl-1-naphthalene, 2,3-dimethyl-1-naphthalene, 3,8-dimethyl-1-naphthalene, 4,8-dimethyl-1-naphthalene, 5,6-dimethyl-1-naphthalene, 2,4-dimethyl-1-naphthalene, 2,3-diethyl-1-naphthalene, 3,4-dipropyl-1-naphthalene, 4,5-dibutyl-1-naphthalene, 5,6-dipentyl-1-naphthalene, 2,4-dihexyl-1-naphthalene, 2,3,6-trimethyl-1-naphthalene, 2,3,4-trimethyl-1-naphthalene, 3,4,5-trimethyl-1-naphthalene, 4,5,6-trimethyl-1-naphthalene, 2,4,8-trimethyl-1-naphthalene, 2,3,6-triethyl-1-naphthalene, 2,3,4-tripropyl-1-naphthalene, 3,4,8-tributyl-1-naphthalene, 4,5,6-tripentyl-1-naphthalene or 2,4,6-trihexyl-1-naphthalene ring; an aryl ring which is substituted with a halogen atom such as, for example, a 4-fluorobenzene, 2-fluorobenzene, 3-fluorobenzene, 4-bromobenzene, 2-iodobenzene, 3-chlorobenzene, 4-chlorobenzene, 3,5-difluorobenzene, 2,5-difluorobenzene, 2,5-diiodobenzene, 2,6-difluorobenzene, 2,4-difluorobenzene, 2,3-dichlorobenzene, 3,4-dichlorobenzene, 2,5-dichlorobenzene, 2,6-dichlorobenzene, 2,4- dibromobenzene, 2,3,6-trifluorobenzene, 2,3,4-trifluorobenzene, 3,4,5-trifluorobenzene, 2,5,6-trifluorobenzene, 2,4,6-trifluorobenzene, 2,3,6-trichlorobenzene, 2,3,4-trichlorobenzene, 3,4,5-tribromobenzene, 2,5,6-tribromobenzene, 2,4,6-tribromobenzene, 1-fluoro-2-naphthalene, 2-fluoro-1-naphthalene, 3-fluoro-1-naphthalene, 2-chloro-1-naphthalene, 1-chloro-2-naphthalene, 2-bromo-1-naphthalene, 3-bromo-1-naphthalene, 2,3-difluoro-1-naphthalene, 3,8-difluoro-1-naphthalene, 4,8-difluoro-1-naphthalene, 5,6-difluoro-1-naphthalene, 2,4-difluoro-1-naphthalene, 2,3-dichloro-1-naphthalene, 3,4-dichloro-1-naphthalene, 4,5-dichloro-1-naphthalene, 5,6-dibromo-1-naphthalene, 2,4-dibromo-1-naphthalene, 2,3,6-trifluoro-1-naphthalene, 2,3,4-trifluoro-1-naphthalene, 3,4,5-trifluoro-1-naphthalene, 4,5,6-trifluoro-1-naphthalene, 2,4,8-trifluoro-1-naphthalene, 2,3,6-trichloro-1-naphthalene, 2,3,4-trichloro-1-naphthalene 3,4,8-tribromo-1-naphthalene, 4,5,6-tribromo-1-naphthalene or 2,4,6-tribromo-1-naphthalene ring; an aryl ring which is substituted with a lower alkoxy group such as, for example, a 4-methoxybenzene, 2-methoxybenzene, 3-methoxybenzene, 4-ethoxybenzene, 4-propoxybenzene, 2-butoxybenzene, 3-ethoxybenzene, 3,5-dimethoxybenzene, 2,5-dimethoxybenzene, 2,5-dipropoxybenzene, 2,6-dimethoxybenzene, 2,4-dimethoxybenzene, 2,3-diethoxybenzene, 3,4-diethoxybenzene, 2,5-diethoxybenzene, 2,6-diethoxybenzene, 2,4-dipropoxybenzene, 2,3,6-trimethoxybenzene, 2,3,4-trimethoxybenzene, 3,4,5-trimethoxybenzene, 2,5,6-methoxybenzene, 2,4,6-trimethoxybenzene, 2,3,6-triethoxybenzene, 2,3,4-triethoxybenzene, 3,4,5-tripropoxybenzene, 2,5,6-tripropoxybenzene, 2,4,6-tripropoxybenzene, 1-methoxy-2-naphthalene, 2-methoxy-1-naphthalene, 3-methoxy-1-naphthalene, 2-ethoxy-1-naphthalene, 1-ethoxy-2-naphthalene, 2-propoxy-1-naphthalene, 3-propoxy-1-naphthalene, 2,3-dimethoxy-1-naphthalene, 3,8-dimethoxy-1-naphthalene, 4,8-dimethoxy-1-naphthalene, 5,6-dimethoxy-1-naphthalene, 2,4-dimethoxy-1-naphthalene, 2,3-dimethoxy-1-naphthalene, 3,4-diethoxy-1-naphthalene, 4,5-diethoxy-1-naphthalene, 5,6-dipropoxy-1-naphthalene, 2,4-dipropoxy-1-naphthalene, 2,3,6-trimethoxy-1-naphthalene, 2,3,4-trimethoxy-1-naphthalene, 3,4,5-trimethoxy-1-naphthalene, 4,5,6-trimethoxy-1-naphthalene, 2,4,8-trimethoxy-1-naphthalene, 2,3,6-triethoxy-1-naphthalene, 2,3,4-triethoxy-1-naphthalene, 3,4,8-tripropoxy-1-naphthalene, 4,5,6-tripropoxy-1-naphthalene or 2,4,6-tripropoxy-1-naphthalene ring; an heteroaryl ring which is unsubstituted, such as, for example, a thiophene or furan ring; an heteroaryl ring which is substituted with an alkyl group such as, for example, a 4-methylthiophene, 2-methylthiophene, 3-methylthiophene, 4-ethylthiophene, 4-butylthiophene, 2-propylthiophene, 3-hexylthiophene, 2,3-dimethylthiophene, 3,4-dimethylthiophene, 2,5-dimethylthiophene, 2,4-dimethylthiophene, 2,3-diethylthiophene, 3,4-dipropylthiophene, 2,5-dibutylthiophene, 2,4-dihexylthiophene, 2,3,4-trimethylthiophene, 3,4,5-trimethylthiophene, 2,3,4-tripropylthiophene, 3,4,5-tributylthiophene; an heteroaryl ring which is substituted with a halogen atom such as, for example, a 4-fluorothiophene, 2-fluorothiophene, 3-fluorothiophene, 4-bromothiophene, 2-iodothiophene, 3-chlorothiophene, 3,5-difluorothiophene, 2,5-difluorothiophene, 2,5-diiodothiophene, 2,4-difluorothiophene, 2,3-dichlorothiophene, 3,4-dichlorothiophene, 2,5-dichlorothiophene, 2,4-dibromothiophene, 2,3,4-trifluorothiophene, 3,4,5-trifluorothiophene, 2,3,4-trichlorothiophene, or 3,4,5-tribromothiophene ring; an heteroaryl ring which is substituted with a lower alkoxy group such as, for example, a 4-methoxythiophene, 2-methoxythiophene, 3-methoxythiophene, 4-ethoxythiophene, 4-propoxythiophene, 2-butoxythiophene, 3-ethoxythiophene, 3,5-dimethoxythiophene, 2,5-dimethoxythiophene, 2,5-dipropoxythiophene, 2,4-dimethoxythiophene, 2,3-diethoxythiophene, 3,4-diethoxythiophene, 2,5-diethoxythiophene, 2,4-dipropoxythiophene, 2,3,4-trimethoxythiophene, 3,4,5-trimethoxythiophene, 2,3,4-triethoxythiophene, or 3,4,5-tripropoxythiophene ring; an aryl ring which is substituted with an alkylthio group such as, for example, a 4-methylthiobenzene, 2-methylthiobenzene, 3-methylthiobenzene, 4-ethylthiobenzene, 4-butylthiobenzene, 2-propylthiobenzene, or 3-hexylthiobenzene ring; an heteroaryl ring which is substituted with an alkylthio group such as, for example, a 4-methylthiothiophene, 2-methylthiothiophene, 3-methylthiothiophene, 4-ethylthiothiophene, or 4-butylthiothiophene ring; an aryl ring which is substituted with a hydroxy group such as, for example, a 4-hydroxybenzene, 2-hydroxybenzene, or 3-hydroxybenzene ring; an heteroaryl ring which is substituted with a hydroxy group such as, for example, a 4-hydroxythiophene, 2-hydroxythiophene, 3-hydroxythiophene ring; an aryl ring which is substituted with a nitro group such as, for example, a 4-nitrobenzene, 2-nitrobenzene, or 3-nitrobenzene ring; or an heteroaryl ring which is substituted with a nitro group such as, for example, a 4-nitrothiophene, 2-nitrothiophene, 3-nitrothiophene ring. Preferred examples for the ring A include an aryl or heteroaryl ring which is not substituted, or a benzene or thiophene ring substituted by one or more halogen atoms such as a fluorine or chlorine atom; by one or more $C_1$-$C_3$ alkyl groups such as a methyl or ethyl group; by a $C_1$-$C_3$ alkoxy group such as a methoxy or ethoxy; by a hydroxy group; by a nitro group; or by a $C_1$-$C_3$ alkylthio group such as a methylthio group.

$R^3$ is a hydrogen atom or a $C_1$-$C_6$ alkyl group and $R^4$ is a hydrogen atom. In this case, it is preferred that $R^3$ is a hydrogen atom or a $C_1$-$C_3$ alkyl group and $R^4$ is a hydrogen atom, and more preferred that both $R^3$ and $R^4$ represent hydrogen atoms. $R^3$ and $R^4$ can alternatively together represent a group of formula (IV):

(wherein each $R^a$ and $R^b$ represents hydrogen or a $C_1$-$C_3$ alkyl group, provided that there are not more than three alkyl groups in the group of formula (IV), m represents 1, 2, or 3, and Y represents two hydrogen atoms or an oxygen atom). In this case, the compounds of formula (I) are then of the general formula (Ia):

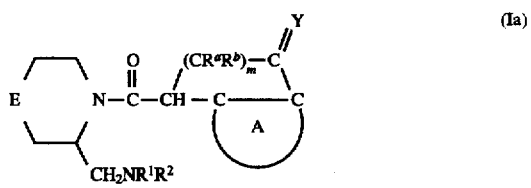

In the formulae (Ia) and (IV), both $R^a$ and $R^b$ preferably represent hydrogen atoms, and m is preferably 1 or 2.

The present invention further embraces pharmaceutically acceptable non-toxic salts of the compounds of general formula (I). Examples of suitable salts include acid addition salts with an inorganic acid for instance a hydrohalogenated acid such as hydrofluoric acid, hydrochloric acid, hydrobromic acid or hydroiodic acid, or nitric acid, perchloric acid, sulfuric acid, phosphoric acid or the like acid; and acid addition salts with an organic acid for instance a lower alkyl sulfonic acid such as methanesulfonic acid, trifluoromethanesulfonic acid or ethanesulfonic acid, an aryl sulfonic acid such as benzenesulfonic acid or p-toluenesulfonic acid, an amino acid such as glutamic acid or aspargic acid, or an organic carboxylic acid such as fumaric acid, succinic acid, citric acid, tartaric acid, oxalic acid, mandelic acid, maleic acid or the like acid.

The compounds of general formula (I) exist in more than one stereoisomeric form, and this invention embraces individual isomers as well as mixtures. It will often be the case that one stereoisomer is more active than another, as may be determined by routine testing.

Preferred isomers of this invention include those compounds and salts wherein the group E is a methylene group and the configuration at the carbon having the substituent —$CH_2NR^1R^2$ is the (S) configuration;

the group E is a sulphur atom and the configuration at the carbon having the substituent —$CH_2NR^1R^2$ is the (R) configuration;

the group E is an oxygen atom and the configuration at the carbon having the substituent —$CH_2NR^1R^2$ is the (R) configuration; or the group E is an optionally substituted imino group and the configuration at the carbon having the substituent —$CH_2NR^1R^2$ has the chirality corresponding to the (R) configuration for the case where E is an imino group and the substituent is —$CH_2NH_2$. In this last respect, the nomenclature for the configuration at the carbon having the substituent —$CH_2NR^1R^2$ for compounds with the preferred chirality will be (R) or (S), depending on the nature of the imino substituent, the group $R^1$ and the group $R^2$.

Furthermore, the compounds of this invention may exist as solvates, particularly hydrates, and this invention extends to such solvates.

Compounds of the general formula (I) in accordance with the present invention are exemplified by the following compounds, by their salts, especially the hydrochloride or methanesulfonate salts, and by their individual diastereoisomers and their individual optical isomers.

1. 1-(indan-1-carbonyl)-2-(pyrrolidin-1-ylmethyl)piperidine
2. 1-(3-oxoindan-1-carbonyl)-2-(pyrrolidin-1-ylmethyl) piperidine
3. 1-(5-chloro-3-oxoindan-1-carbonyl)-2-(pyrrolidin-1-ylmethyl)piperidine
4. 1-(5-methyl-3-oxoindan-1-carbonyl)-2-(pyrrolidin-1-ylmethyl)piperidine
5. 1-(5-nitro-3-oxoindan-1-carbonyl)-2-(pyrrolidin-1-ylmethyl)piperidine
6. 1-(5-methoxy-3-oxoindan-1-carbonyl)-2-(pyrrolidin-1-ylmethyl)piperidine
7. 1-(6-chloro-3-oxoindan-1-carbonyl)-2-(pyrrolidin-1-ylmethyl)piperidine
8. 1-(6-methoxy-3-oxoindan-1-carbonyl)-2-(pyrrolidin-1-ylmethyl)piperidine
9. 1-(5,6-dichloro-3-oxoindan-1-carbonyl)-2-(pyrrolidin-1-ylmethyl)piperidine
10. 1-(4,5-dichloro-3-oxoindan-1-carbonyl)-2-(pyrrolidin-1-ylmethyl)piperidine
11. 1-(6-hydroxy-3-oxoindan-1-carbonyl)-2-(pyrrolidin-1-ylmethyl)piperidine
12. 4-(5-methyl-3-oxoindan-1-carbonyl)-3-(pyrrolidin-1-ylmethyl)morpholine
13. 4-(6,7-dichloro-1,2,3,4-tetrahydronaphthoyl)-3-(piperidinomethyl)thiomorpholine
14. 1-(5,6-dichloroindan-1-carbonyl)-2-(piperidinomethyl)piperidine
15. 1-(3-oxoindan-1-carbonyl)-2-(piperidinomethyl)piperidine
16. 1-(5,6-dichloro-3-oxoindan-1-carbonyl)-2-(piperidinomethyl)piperidine
17. 2-(pyrrolidin-1-ylmethyl)-1-(1,2,3,4-tetrahydro-4-oxo-1-naphthoyl)piperidine
18. 1-(6,7-dichloro-1,2,3,4-tetrahydro-4-oxo-1-naphthoyl)-2-(pyrrolidin-1-ylmethyl)piperidine
19. 4,5-dihydro-6-oxo-4-[2-(pyrrolidin-1-ylmethyl) piperidine-1-carbonyl]-6H-cyclopenta[b]thiophene
20. 4,5-dihydro-6-oxo-4-[2-(pyrrolidin-1-ylmethyl) piperidine-1-carbonyl]-6H-cyclopenta[b]furan
21. 2-chloro-4,5-dihydro-6-oxo-4-[2-(pyrrolidin-1-ylmethyl)piperidine-1-carbonyl]-6H-cyclopenta[b] thiophene
22. 1-(5,6-dichloro-3-oxoindan-1-carbonyl)-2-(4-methylpiperazin-1-ylmethyl)piperidine
23. 4-[2-(3,4-dichlorophenyl)propionyl]-3-(pyrrolidin-1-ylmethyl)thiomorpholine
24. 4-[2-(3,4-dichlorophenyl)propionyl]-3-(pyrrolidin-1-ylmethyl)morpholine
25. 4,5-dihydro-6-oxo-4-[3-(pyrrolidin-1-ylmethyl) thiomorpholine-4-carbonyl]-6H-cyclopenta[b]thiophene
26. 4,5-dihydro-4-[3-(pyrrolidin-1-ylmethyl) thiomorpholine-4-carbonyl]-6H-cyclopenta[b]thiophene
27. 4,5-dihydro-6-oxo-4-[3-(pyrrolidin-1-ylmethyl) thiomorpholine-4-carbonyl]-6H-cyclopenta[b]furan
28. 4,5,6,7-tetrahydro-7-oxo-4-[3-(pyrrolidin-1-ylmethyl) thiomorpholine-4-carbonyl]benzo[b]thiophene
29. 4-(2,2-dimethyl-3-oxoindan-1-carbonyl)-3-(pyrrolidin-1-ylmethyl)thiomorpholine
30. 4-(3,4-dichlorophenylacetyl)-3-(pyrrolidin-1-ylmethyl) thiomorpholine
31. 4-(4-chlorophenylacetyl)-3-(pyrrolidin-1-ylmethyl) thiomorpholine
32. 4-(4-methylphenylacetyl)-3-(pyrrolidin-1-ylmethyl) thiomorpholine
33. 4-(4-methoxyphenylacetyl)-3-(pyrrolidin-1-ylmethyl) thiomorpholine
34. 4-(4-methylthiophenylacetyl)-3-(pyrrolidin-1-ylmethyl) thiomorpholine
35. 4-(4-nitrophenylacetyl)-3-(pyrrolidin-1-ylmethyl) thiomorpholine
36. 4-(3,4-dichlorophenylacetyl)-3-(pyrrolidin-1-ylmethyl) morpholine
37. 4-(4-chlorophenylacetyl)-3-(pyrrolidin-1-ylmethyl) morpholine
38. 4-(4-methylphenylacetyl)-3-(pyrrolidin-1-ylmethyl) morpholine
39. 4-(4-methoxyphenylacetyl)-3-(pyrrolidin-1-ylmethyl) morpholine
40. 4-(4-methylthiophenylacetyl)-3-(pyrrolidin-1-ylmethyl) morpholine
41. 4-(4-nitrophenylacetyl)-3-(pyrrolidin-1-ylmethyl) morpholine
42. 1-(3,4-dichlorophenylacetyl)-4-methyl-2-(pyrrolidin-1-ylmethyl)piperazine
43. 1-(4-chlorophenylacetyl)-4-methyl-2-(pyrrolidin-1-ylmethyl)piperazine 44. 4-methyl-1-(4-methylphenylacetyl)-2-(pyrrolidin-1-ylmethyl)piperazine
45. 1-(4-methoxyphenylacetyl)-4-methyl-2-(pyrrolidin-1-ylmethyl)piperazine
46. 4-methyl-1-(4-methylthiophenylacetyl)-2-(pyrrolidin-1-ylmethyl)piperazine
47. 4-methyl-1-(4-nitrophenylacetyl)-2-(pyrrolidin-1-ylmethyl)piperazine
48. 4-(4-biphenylacetyl)-3-(pyrrolidin-1-ylmethyl)thiomorpholine
49. 4-(3,4-dichlorophenylacetyl)-3-(piperidinomethyl)thiomorpholine
50. 4-(3,4-dichlorophenylacetyl)-3-(morpholinomethyl)thiomorpholine
51. 3-(pyrrolidin-1-ylmethyl)-4-(2-thienylacetyl)thiomorpholine
52. 4-(1-naphthylacetyl)-3-(pyrrolidin-1-ylmethyl)thiomorpholine
53. 4-(3-pyridylacetyl)-3-(pyrrolidin-1-ylmethyl)thiomorpholine
54. 4-(4-biphenylacetyl)-3-(pyrrolidin-1-ylmethyl)morpholine
55. 4-(3,4-dichlorophenylacetyl)-3-(piperidinomethyl)morpholine
56. 4-(3,4-dichlorophenylacetyl)-3-(morpholinomethyl)morpholine
57. 3-(pyrrolidin-1-ylmethyl)-4-(2-thienylacetyl)morpholine
58. 4-(1-naphthylacetyl)-3-(pyrrolidin-1-ylmethyl)morpholine
59. 4-(3-pyridylacetyl)-3-(pyrrolidin-1-ylmethyl)morpholine
60. 4-methyl-2-(pyrrolidin-1-ylmethyl)-1-(2-thienylacetyl)piperazine
61. 4-methyl-1-(1-naphthylacetyl)-2-(pyrrolidin-1-ylmethyl)piperazine
62. 4-methyl-1-(3-pyridylacetyl)-2-(pyrrolidin-1-ylmethyl)piperazine
63. 4-(3,4-dichlorophenylacetyl)-3-(dimethylaminomethyl)thiomorpholine
64. 4-(3,4-dichlorophenylacetyl)-3-(dimethylaminomethyl)morpholine
65. 4-(3,4-difluorophenylacetyl)-3-(pyrrolidin-1-ylmethyl)morpholine
66. 4-(3,4-dichlorophenylacetyl)-3-(4-methylpiperazin-1-ylmethyl)morpholine
67. 4-(indan-1-carbonyl)-3-(pyrrolidin-1-ylmethyl)thiomorpholine
68. 4-(3-oxoindan-1-carbonyl)-3-(pyrrolidin-1-ylmethyl)thiomorpholine
69. 4-(5-chloroindan-1-carbonyl)-3-(pyrrolidin-1-ylmethyl)thiomorpholine
70. 4-(5-chloro-3-oxoindan-1-carbonyl)-3-(pyrrolidin-1-ylmethyl)thiomorpholine
71. 4-(5-isopropylindan-1-carbonyl)-3-(pyrrolidin-1-ylmethyl)thiomorpholine
72. 4-(5-methylindan-1-carbonyl)-3-(pyrrolidin-1-ylmethyl)thiomorpholine
73. 4-(5-methyl-3-oxoindan-1-carbonyl)-3-(pyrrolidin-1-ylmethyl)thiomorpholine
74. 4-(5-methoxyindan-1-carbonyl)-3-(pyrrolidin-1-ylmethyl)thiomorpholine
75. 4-(5-methoxy-3-oxoindan-1-carbonyl)-3-(pyrrolidin-1-ylmethyl)thiomorpholine
76. 4-(5-isopropyl-3-oxoindan-1-carbonyl)-3-(pyrrolidin-1-ylmethyl)thiomorpholine
77. 4-(7-chloro-1,2,3,4-tetrahydro-4-oxo-1-naphthoyl)-3-(pyrrolidin-1-ylmethyl)thiomorpholine
78. 4-(7-chloro-1,2,3,4-tetrahydro-1-naphthoyl)-3-(pyrrolidin-1-ylmethyl)thiomorpholine
79. 4-(6,7-dichloro-1,2,3,4-tetrahydro-4-oxo-1-naphthoyl)-3-(pyrrolidin-1-ylmethyl)thiomorpholine
80. 4-(6,7-dichloro-1,2,3,4-tetrahydro-1-naphthoyl)-3-(pyrrolidin-1-ylmethyl)thiomorpholine
81. 4-(7-chloro-1,2,3,4-tetrahydro-4-oxo-1-naphthoyl)-3-(morpholinomethyl)thiomorpholine
82. 4-(7-chloro-1,2,3,4-tetrahydro-1-naphthoyl)-3-(morpholinomethyl)thiomorpholine
83. 4-(6,7-dichloro-1,2,3,4-tetrahydro-4-oxo-1-naphthoyl)-3-(morpholinomethyl)thiomorpholine
84. 4-(6,7-dichloro-1,2,3,4-tetrahydro-1-naphthoyl)-3-(morpholinomethyl)thiomorpholine
85. 4-(6,7-difluoro-1,2,3,4-tetrahydro-4-oxo-1-naphthoyl)-3-(pyrrolidin-1-ylmethyl)thiomorpholine
86. 4-(6,7-difluoro-1,2,3,4-tetrahydro-1-naphthoyl)-3-(pyrrolidin-1-ylmethyl)thiomorpholine
87. 3-(pyrrolidin-1-ylmethyl)-4-(1,2,3,4-tetrahydro-7-methyl-4-oxo-1-naphthoyl)thiomorpholine
88. 3-(pyrrolidin-1-ylmethyl)-4-(1,2,3,4-tetrahydro-7-methyl-1-naphthoyl)thiomorpholine
89. 3-(pyrrolidin-1-ylmethyl)-4-(1,2,3,4-tetrahydro-7-isopropyl-4-oxo-1-naphthoyl)thiomorpholine
90. 3-(pyrrolidin-1-ylmethyl)-4-(1,2,3,4-tetrahydro-7-isopropyl-1-naphthoyl)thiomorpholine
91. 4-(1,2,3,4-tetrahydro-7-methyl-4-oxo-1-naphthoyl)-3-(morpholinomethyl)thiomorpholine
92. 3-(morpholinomethyl)-4-(1,2,3,4-tetrahydro-7-methyl-1-naphthoyl)thiomorpholine
93. 3-(morpholinomethyl)-4-(1,2,3,4-tetrahydro-4-oxo-1-naphthoyl)thiomorpholine
94. 3-(morpholinomethyl)-4-(1,2,3,4-tetrahydro-1-naphthoyl)thiomorpholine
95. 4-(5,6-dichloroindan-1-carbonyl)-3-(morpholinomethyl)thiomorpholine
96. 4-(5,6-dichloroindan-1-carbonyl)-3-(4-methylpiperazin-1-ylmethyl)thiomorpholine
97. 4-(5,6-dichloro-3-oxoindan-1-carbonyl)-3-(morpholinomethyl)thiomorpholine
98. 4-(5,6-dichloro-3-oxoindan-1-carbonyl)-3-(4-methylpiperazin-1-ylmethyl)thiomorpholine
99. 4-(indan-1-carbonyl)-3-(piperidinomethyl)thiomorpholine
100. 4-(3-oxoindan-1-carbonyl)-3-(piperidinomethyl)thiomorpholine
101. 4-(5-chloroindan-1-carbonyl)-3-(piperidinomethyl)thiomorpholine
102. 4-(5-chloro-3-oxoindan-1-carbonyl)-3-(piperidinomethyl)thiomorpholine
103. 4-(6-chloroindan-1-carbonyl)-3-(piperidinomethyl)thiomorpholine
104. 4-(5-methylindan-1-carbonyl)-3-(piperidinomethyl)thiomorpholine
105. 4-(5-methyl-3-oxoindan-1-carbonyl)-3-(piperidinomethyl)thiomorpholine
106. 4-(5-isopropylindan-1-carbonyl)-3-(piperidinomethyl)thiomorpholine
107. 4-(5-isopropyl-3-oxoindan-1-carbonyl)-3-(piperidinomethyl)thiomorpholine
108. 4-(6-chloro-3-oxoindan-1-carbonyl)-3-(piperidinomethyl)thiomorpholine
109. 4-(6-chloroindan-1-carbonyl)-3-(pyrrolidin-1-ylmethyl)thiomorpholine
110. 4-(6-chloro-3-oxoindan-1-carbonyl)-3-(pyrrolidin-1-ylmethyl)thiomorpholine
111. 4-(6-methylindan-1-carbonyl)-3-(pyrrolidin-1-ylmethyl)thiomorpholine 112. 4-(6-methyl-3-oxoindan-1-carbonyl)-3-(pyrrolidin-1-ylmethyl)thiomorpholine
113. 4-(5,6-dichloroindan-1-carbonyl)-3-(pyrrolidin-1-ylmethyl)thiomorpholine
114. 4-(6-methoxyindan-1-carbonyl)-3-(pyrrolidin-1-ylmethyl)thiomorpholine
115. 4-(6-methoxy-3-oxoindan-1-carbonyl)-3-(pyrrolidin-1-ylmethyl)thiomorpholine
116. 4-(6-isopropylindan-1-carbonyl)-3-(pyrrolidin-1-ylmethyl)thiomorpholine
117. 4-(6-isopropyl-3-oxoindan-1-carbonyl)-3-(pyrrolidin-1-ylmethyl)thiomorpholine
118. 4-(5,6-dichloro-3-oxoindan-1-carbonyl)-3-(pyrrolidin-1-ylmethyl)thiomorpholine
119. 3-(piperidinomethyl)-4-(1,2,3,4-tetrahydro-4-oxo-1-naphthoyl)thiomorpholine
120. 3-(piperidinomethyl)-4-(1,2,3,4-tetrahydro-1-naphthoyl)thiomorpholine
121. 4-(6-chloro-1,2,3,4-tetrahydro-4-oxo-1-naphthoyl)-3-(piperidinomethyl)thiomorpholine
122. 4-(6-chloro-1,2,3,4-tetrahydro-1-naphthoyl)-3-(piperidinomethyl)thiomorpholine
123. 3-(piperidinomethyl)-4-(1,2,3,4-tetrahydro-6-methyl-4-oxo-1-naphthoyl)thiomorpholine
124. 3-(piperidinomethyl)-4-(1,2,3,4-tetrahydro-6-methyl-1-naphthoyl)thiomorpholine
125. 4-(3-oxoindan-1-carbonyl)-3-(pyrrolidin-1-ylmethyl)morpholine
126. 4-(5-chloro-3-oxoindan-1-carbonyl)-3-(pyrrolidin-1-ylmethyl)morpholine
127. 4-(5,6-dichloro-3-oxoindan-1-carbonyl)-3-(pyrrolidin-1-ylmethyl)morpholine
128. 3-(pyrrolidin-1-ylmethyl)-4-(1,2,3,4-tetrahydro-4-oxo-1-naphthoyl)morpholine
129. 3-(pyrrolidin-1-ylmethyl)-4-(1,2,3,4-tetrahydro-1-naphthoyl)morpholine
130. 4-(6,7-dichloro-1,2,3,4-tetrahydro-4-oxo-1-naphthoyl)-3-(pyrrolidin-1-ylmethyl)morpholine
131. 4-(6,7-dichloro-1,2,3,4-tetrahydro-1-naphthoyl)-3-(pyrrolidin-1-ylmethyl)morpholine
132. 4-(5-chloro-3-oxoindan-1-carbonyl)-3-(dimethylaminomethyl)morpholine
133. 4-methyl-1-(3-oxoindan-1-carbonyl)-2-(pyrrolidin-1-ylmethyl)piperazine
134. 1-(indan-1-carbonyl)-4-methyl-2-(pyrrolidin-1-ylmethyl)piperazine
135. 3-(pyrrolidin-1-ylmethyl)-4-(1,2,3,4-tetrahydro-4-oxo-1-naphthoyl)thiomorpholine
136. 3-(pyrrolidin-1-ylmethyl)-4-(1,2,3,4-tetrahydro-1-naphthoyl)thiomorpholine
137. 4-(6-chloro-1,2,3,4-tetrahydro-4-oxo-1-naphthoyl)-3-(pyrrolidin-1-ylmethyl)thiomorpholine
138. 4-(6-chloro-1,2,3,4-tetrahydro-1-naphthoyl)-3-(pyrrolidin-1-ylmethyl)thiomorpholine
139. 3-(pyrrolidin-1-ylmethyl)-4-(1,2,3,4-tetrahydro-6-methyl-4-oxo-1-naphthoyl)thiomorpholine
140. 3-(pyrrolidin-1-ylmethyl)-4-(1,2,3,4-tetrahydro-6-methyl-1-naphthoyl)thiomorpholine
141. 3-(pyrrolidin-1-ylmethyl)-4-(1,2,3,4-tetrahydro-6-isopropyl-4-oxo-1-naphthoyl)thiomorpholine
142. 3-(pyrrolidin-1-ylmethyl)-4-(1,2,3,4-tetrahydro-6-isopropyl-1-naphthoyl)thiomorpholine
143. 4-(5,6-difluoroindan-1-carbonyl)-3-(pyrrolidin-1-ylmethyl)thiomorpholine
144. 4-(5,6-difluoro-3-oxoindan-1-carbonyl)-3-(pyrrolidin-1-ylmethyl)thiomorpholine
145. 4-(5,6-dimethylindan-1-carbonyl)-3-(pyrrolidin-1-ylmethyl)thiomorpholine
146. 4-(5,6-dimethyl-3-oxoindan-1-carbonyl)-3-(pyrrolidin-1-ylmethyl)thiomorpholine
147. 4-(6-methylindan-1-carbonyl)-3-(piperidinomethyl)thiomorpholine
148. 4-(6-methyl-3-oxoindan-1-carbonyl)-3-(piperidinomethyl)thiomorpholine
149. 4-(6-isopropylindan-1-carbonyl)-3-(piperidinomethyl)thiomorpholine
150. 4-(6-isopropyl-3-oxoindan-1-carbonyl)-3-(piperidinomethyl)thiomorpholine
151. 4-(5,6-dichloroindan-1-carbonyl)-3-(piperidinomethyl)thiomorpholine
152. 4-(5,6-dimethylindan-1-carbonyl)-3-(piperidinomethyl)thiomorpholine
153. 4-(5,6-dimethyl-3-oxoindan-1-carbonyl)-3-(piperidinomethyl)thiomorpholine
154. 4-(5,6-difluoroindan-1-carbonyl)-3-(piperidinomethyl)thiomorpholine
155. 4-(5,6-difluoro-3-oxoindan-1-carbonyl)-3-(piperidinomethyl)thiomorpholine
156. 4-(5,6-dichloro-3-oxoindan-1-carbonyl)-3-(piperidinomethyl)thiomorpholine
157. 1-(5-chloro-3-oxoindan-1-carbonyl)-4-methyl-2-(pyrrolidin-1-ylmethyl)piperazine
158. 1-(5-chloroindan-1-carbonyl)-4-methyl-2-(pyrrolidin-1-ylmethyl)piperazine
159. 4-(5-chloroindan-1-carbonyl)-3-(pyrrolidin-1-ylmethyl)morpholine
160. 4-methyl-2-(pyrrolidin-1-ylmethyl)-1-(1,2,3,4-tetrahydro-4-oxo-1-naphthoyl)piperazine
161. 4-methyl-2-(pyrrolidin-1-ylmethyl)-1-(1,2,3,4-tetrahydro-1-naphthoyl)piperazine
162. 1-(5,6-dichloro-3-oxoindan-1-carbonyl)-4-methyl-2-(pyrrolidin-1-ylmethyl)piperazine
163. 1-(5,6-dichloroindan-1-carbonyl)-4-methyl-2-(pyrrolidin-1-ylmethyl)piperazine
164. 1-(6-chloro-1,2,3,4-tetrahydro-4-oxo-1-naphthoyl)-4-methyl-2-(pyrrolidin-1-ylmethyl)piperazine
165. 1-(1,2,3,4-tetrahydro-6-chloro-1-naphthoyl)-4-methyl-2-(pyrrolidin-1-ylmethyl)piperazine
166. 1-(5-methyl-3-oxoindan-1-carbonyl)-4-methyl-2-(pyrrolidin-1-ylmethyl)piperazine
167. 4-(5-methyl-3-oxoindan-1-carbonyl)-3-(pyrrolidin-1-ylmethyl)piperazine
168. 1-(6,7-dichloro-1,2,3,4-tetrahydro-4-oxo-1-naphthoyl)-4-methyl-2-(pyrrolidin-1-ylmethyl)piperazine
169. 1-(6,7-dichloro-1,2,3,4-tetrahydro-1-naphthoyl)-4-methyl-2-(pyrrolidin-1-ylmethyl)piperazine
170. 4-(5,6-dichloro-3-oxoindan-1-carbonyl)-3-(morpholinomethyl)morpholine
171. 4-(6,7-dichloro-4-oxo-1,2,3,4-tetrahydro-1-naphthoyl)-3-(piperidinomethyl)thiomorpholine
172. 1-(5-methylthio-3-oxoindan-1-carbonyl)-3-(pyrrolidin-1-ylmethyl)thiomorpholine
173. 1-(5,6-dichloroindan-1-carbonyl)-2-(pyrrolidin-1-ylmethyl)piperidine
174. 1-(5,6-dichloro-3-oxoindan-1-carbonyl)-2-(morpholinomethyl)piperidine
175. 4-[2-(3,4-dichlorophenyl)propionyl]-3-(pyrrolidin-1-ylmethyl)thiomorpholine
176. 4-(5-trifluoromethyl-3-oxoindan-1-carbonyl)-3-(pyrrolidin-1-ylmethyl)thiomorpholine Preferred compounds within this list include Compound Numbers 1, 2, 4, 9, 10, 13, 14, 16, 17, 19, 20, 23, 24, 25, 26, 28, 30, 32, 36, 38, 42, 44, 49, 50, 51, 55, 56, 57, 60, 63, 64, 65, 68, 69, 70, 71, 72, 73, 79, 80, 81, 82, 83, 84, 85, 86, 87, 88, 91, 95, 96, 97, 98, 99, 102, 104, 105, 110, 111, 112, 113, 118, 119, 120, 121, 123, 125, 126, 127, 130, 131, 132, 135, 136, 137, 138, 139, 140, 143, 144, 147, 148, 151, 154, 155, 156, 160, 162, 164, 168, 170, 171, 172, 173 and 175 and their salts, especially their hydrochlorides, and their isomeric forms.

More preferred compounds within this list include Compound Numbers 9, 10, 13, 14, 17, 23, 30, 32, 49, 63, 72, 73, 79, 80, 102, 105, 110, 113, 118, 123, 127, 130, 137, 139, 144, 147, 148, 151, 156, 162, and 171, and their salts, especially their hydrochlorides, and their isomeric forms.

Most preferred compounds within this list include Compound Numbers 9, 13, 30, 72, 73, 79, 80, 113, 118, 151, 156, and 171, and their salts, especially their hydrochlorides, and their isomeric forms.

The novel carboxylic acid amide derivatives of this invention, including the acid addition salts, exhibit useful pharmacological effects, such as anti-inflammatory and analgesic activity.

The pharmacological activity of compounds of this invention was examined according to recognised procedures.

p-Phenylquinone-induced writhing in mice

Testing was performed essentially according to the procedure of Siegmund et al. reported in Proceedings of Society for Experimental Biology & Medicine 95, 729 (1957).

Male ddY mice (Japan SLC) each weighing about 20 g were divided into groups each including from 5 to 10 mice, and were fasted for 16 hours from the day before the test. A compound to be tested was dissolved in physiological saline, and injected subcutaneously. After 15 minutes, 0.1 ml/mouse of 0.03% p-phenylquinone was injected intraperitoneally. Five minutes later, the frequency of writhing reactions in the mouse was counted for the following 10 minutes. For the control mice, only physiological saline solution was injected. Mice in which the frequency of writhing reactions was decreased to a half or less of the mean frequency of writhing reactions in the control mice were regarded as analgesic-effective mice. The ratio, analgesic-effective animals/all animals, was obtained for every dosage, and then $ED_{50}$ values (50% effective dose) were calculated according to the probit method. For some test compounds the test was modified to determine the writhing effect at a dose of 320 µg/kg.

Affinity to receptors

A raw preparation from brain membrane was made according to the method of Pasuternak et al. [Molecular Pharmacology 11, 340 (1975)]. The whole brains were taken from male Hartley guinea pigs each weighing from 400 to 700 g (Japan SLC) and the cerebella were removed. One part of the whole brain sample was homogenized in 30 parts of ice-cooled 50 mM Tris buffer solution (pH 7.4) by use of a Polytron homogenizer, and then, centrifuged for 15 minutes at 49,000×g. The precipitated pellet was suspended in the same kind of buffer. The suspension was incubated for 30 minutes at 37° C. and centrifuged for 15 minutes at 49,000× g. One part of the precipitate was suspended in 30 parts of the buffer solution, and preserved at −80° C. Before use, the suspension was melted, homogenized using a Dounce-type homogenizer, and diluted to a final protein concentration of 0.5 mg/ml.

Binding to κ-receptors was tested essentially according to the method reported in Archives of Pharmacology 319, 197 (1982) by Magnan et al. Taking 0.6 nM of tritium-labelled ethylketocyclazocine as a labelled ligand, binding to the brain membranous preparation was examined by addition of 100 nM of DAGO (D-Ala$^2$, MePhe$^4$, Gly-ol$^5$ enkephalin) and 10 nM of DADLE ([D-Ala$^2$, D-Leu$^5$]-enkephalin) to saturate the µ- and δ-receptors. The membranous preparation, labelled ligand, cold ligand and compound to be tested were incubated in 1 ml of Tris buffer at 25° C. for 45 minutes. Then, the mixture was mixed with 5 ml of ice-cooled buffer solution, filtered through Watmann GF/B filter paper under reduced pressure, and washed twice. The filter paper was placed in a n emulsion scintillator (ACS-II) and allowed to stand overnight, and then the radioactivity was measured by a liquid scintillation counter. The affinity of test compound to the receptor was assessed as the concentration required to inhibit binding of the labelled ligand by 50% ($IC_{50}$, nM).

Binding to µ-receptors was tested according to the procedure of Magnan et al. mentioned above. By using 1 nM of tritium-labelled DAGO as a labelled ligand, the test was carried out in a similar manner to that mentioned in the experiment for testing binding to κ-receptors. The affinity of test compound was assessed as an $IC_{50}$.

The results of the tests are summarized in the following Table, and indicate that compounds of general formula (I), and acid addition salts, are useful as analgesic agents.

TABLE

| Example compound | Analgesic effect Phenylquinone-induced writhing | | Binding to opioid receptors ($IC_{50}$, nM) | |
|---|---|---|---|---|
| | $ED_{50}$ µg/kg s.c. | 320 µg/kg | κ | µ |
| 1 | 6.20 | | 1.75 | 1068 |
| 2-E$_1$ | 1.73 | | 0.90 | 232 |
| 4-D$_1$ | 3.43 | | 1.40 | 531 |
| 2-E$_2$ | 320 | | 258 | 10000 |
| 4-D$_2$ | 270 | | 366 | 10000 |
| 17 | | 5/5 | 1.1 | — |
| 36 | 3.4 | | 2.4 | 1135 |
| 41-D$_1$ | 1.3 | | 0.67 | 698.2 |
| U-50488E | 490 | 2/5 | 9.92 | 636 |
| Morphine HCl | 480 | 2/5 | 552 | 5.1 |

Compound U-50488E is trans-3,4-dichloro-N-methyl-N-[2-(1-pyrrolidinyl)cyclohexyl]benzeneacetamide, see J. Pharmacol. Exp. Ther. (1983) 224, 7

For the administration route of the compounds of this invention, there may be mentioned injection; the oral route using tablets, capsules, granules, powders or syrups; the perintestinal route using suppositories; or the parenteral route using ointments, creams or patches. Though variable depending on the symptoms, age, body weight and other factors, the usual daily dose for an adult person for the typical administration routes is 0.005 mg to 10 mg given by injection. 0.01 to 10 mg given by patches, or 0.1 mg to 100 mg given by oral route. The daily dosage may be given once or divided into several doses.

The novel compounds of the present invention of general formula (I) can be synthesized by conventional processes such as those employed for amide synthesis, using starting materials which are known or which may be prepared by analogy with the preparation of known compounds.

Typically, an acid of general formula (II):

(wherein $R^3$, $R^4$, and ring A are as defined) is reacted optionally in the form of a derivative with an amine of general formula (III):

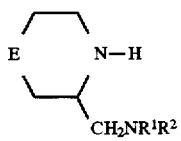

(III)

(wherein $R^1$, $R^2$ and E are as defined).

For example, the acid of the general formula (II) may be employed in the reaction with the amine of the general formula (III) in the form of a derivative which is an acyl halide such as acyl chloride, acyl bromide, or acyl iodide. Such a reaction can be carried out in the presence of a base in an inert solvent. Preferred bases include an organic amine such as triethylamine or DBU; or an inorganic base such as sodium carbonate, potassium carbonate, sodium hydroxide or potassium hydroxide. As appropriate depending mainly on the choice of base, the solvent can be an organic solvent or an aqueous solvent. Preferred organic solvents include a halogenated hydrocarbon such as methylene chloride, chloroform, carbon tetrachloride or 1,2-dichloroethane; or an ether such as diethyl ether, tetrahydrofuran or 1,4-dioxane. Preferred aqueous solvents include water or aqueous organic solvents. For this reaction in the case of using an organic or inorganic base in an organic solvent, the temperature is usually from $-30°$ C. to the reflux temperature of the solvent, more typically from $-10°$ C. to room temperature. On the other hand, for this reaction in the case of using an organic or inorganic base in an aqueous solvent, the temperature is usually from $-5°$ to $0°$ C. Though variable depending on the reaction temperature and the like, the reaction usually takes from 30 minutes to 3 hours.

In another example of synthesis of the present compounds, the acid of the general formula (II) may be employed in the reaction with the amine of the general formula (III) in the form of a derivative which is a mixed acid anhydride. Such an anhydride can readily be obtained by reacting the acid for instance with a haloformate of general formula Hal-COOR$^5$, (where $R^5$ represents a $C_1$–$C_3$ alkyl group such as a methyl or ethyl group, and Hal represents a halogen atom such as a chlorine or bromine atom), in the presence of organic base in an inert solvent to give a mixed acid anhydride. For the solvent, a halogenated hydrocarbon such as methylene chloride, 1,2-dichloroethane, carbon tetrachloride or chloroform, an amide such as dimethylformamide, or an ether such as diethyl ether, tetrahydrofuran or 1,4-dioxane is preferred. For the organic base, a tertiary amine such as triethylamine, N-methylmorpholine or an organic amine such as pyridine is preferred. The reaction is preferably carried out at from $-20°$ C. to the reflux temperature of the solvent employed, and usually requires from 30 minutes to 12 hours. The resulting acid anhydride can then be allowed to react with an amine compound of the general formula (III). Usually this reaction is carried out without isolation of the anhydride from the solvent containing organic base, but more generally the reaction is carried out using conditions similar to those mentioned above for the reaction of an acyl chloride with the amine (III).

In a further example of amide formation, the reaction using a condensing reagent; for example, the Mukaiyama reaction can be employed. This reaction is generally performed in the presence of a condensing reagent such as triphenylphosphine and 2,2'-pyridine disulfide (for a Mukaiyama reaction), or 1,3-dicyclohexylcarbodiimide (DCC), in an inert solvent. The solvent is typically a polar solvent such as an ether, for example tetrahydrofuran, a nitrile, for example acetonitrile, or an amide, for example dimethylformamide. The reaction is normally carried out at from $-20°$ C. to $100°$ C. Though variable depending on the reaction temperature, the reaction usually requires 30 minutes to 24 hours.

Variations in the process employed for production of the compounds of general formula (I) can be adopted. For instance, the acid of the general formula (II) may be employed in the reaction with the amine of the general formula (III) in the form of a derivative which is an appropriately unsaturated acid. Such an unsaturated acid may be reacted with the amine to form an unsaturated amide, which is then reduced to give a compound of formula (I). This method can be generally employed to produce compounds of formula (I) where $R^3$ and $R^4$ represent the group of formula (IV) and thus form a ring fused to ring A. In this instance, the starting acid can have a double bond in the ring fused to the ring A, which double bond may be reduced in conventional manner after amide formation. In particular, for the preparation of 3-oxoindan-1-carbonyl amides, the starting acid may be a 3-oxo-1-indene-1-carboxylic acid which is reacted optionally as a reactive derivative with an amine of general formula (III) and then reduced to convert the indene ring to an indan ring.

After completion of the amide formation, the desired compound of the general formula (I) can be obtained from the reaction mixture by conventional means. The compound can be purified, for example, by chromatography or by preparing an acid addition salt such as a hydrochloride.

In general, the compounds of the general formula (I) can, if desired, be converted into a pharmaceutically acceptable acid addition salt by treatment with an inorganic acid such as hydrochloric acid, hydrobromic acid, hydroiodic acid, sulfuric acid or phosphoric acid, or with an organic acid such as oxalic acid, fumaric acid, maleic acid, mandelic acid, citric acid, tartaric acid, benzenesulfonic acid, p-toluenesulfonic acid, methanesulfonic acid or ethanesulfonic acid.

The compounds of the general formula (I) exist as diastereoisomers and optical isomers, due to the presence of asymmetric carbon atoms in the molecule. If desired, one or more of the isomers of compound (I) can be separated from a mixture of the isomers by a conventional isolation method, or the optical isomers of compound (I) can be obtained by amide formation using an optically resolved starting material of general formula (II) and/or (III).

EXAMPLES OF THE INVENTION

The present invention is illustrated by the following non-limiting Examples, which include a Pharmaceutical Example and a Preparative Example. Some compounds prepared in the Examples are diastereoisomers for which the absolute configuration is not known. For such compounds, prefixes R* or S* are employed, indicating the compound in question is a racemic mixture. Thus, (1S*, 2S*) means a 1:1 mixture of (1R, 2R) and (1S, 2S) and is the same as (1R*, 2R*). Correspondingly, (1R*, 2S*) means a 1:1 mixture of (1R, 2S) and (1S, 2R) and is the same as (1S*, 2R*).

Example 1

1-(5,6-dichloro-3-oxoindan-1-carbonyl)-2-(pyrrolidin-1-ylmethyl)piperidine hydrochloride 3.5 g (21.4 m mol) of 2-(pyrrolidin-1-ylmethyl)piperidine dihydrochloride (synthesized according to the method of U.S. Pat. No. 2,684,965) was added to 85.6 ml (85.6 m mol) of 1N sodium hydroxide solution cooled at from 0° C. to −5° C. The mixture was stirred for 30 minutes, then 20 ml of methylene chloride containing 5.63 g of 5,6-dichloro-3-oxoindan-1-carbonyl chloride (prepared by conventional synthesis from its corresponding acid made according to the procedure reported by Lahiri et al. in J. Indian Chem. Soc. 53, 1041 (1976)) was added dropwise to the mixture. The mixture was stirred for 90 minutes at −5° C., and then for 3 hours at room temperature.

After completion of the reaction, the reaction mixture was poured into ice water and extracted with diethyl ether. The extract was washed with saturated aqueous sodium chloride solution and dried over anhydrous sodium sulfate. The solvent was distilled off and the residue was subjected to column chromatography to obtain 1.31 g of the desired compound by elution with a mixed solvent of ethyl acetate, triethylamine and ethanol (100:1:1). The product was dissolved in acetone, mixed with a 4N 1,4-dioxane solution of hydrogen chloride, evaporated down, and recrystallized from a mixed solvent of ethanol, acetone and diethyl ether (1:1:2), to give 1.24 g of the title compound melting at 239°–242° C. (dec).

Elemental analysis (%) $C_{20}H_{25}Cl_3N_2O_2$ Calcd C, 55.63; H, 5.84; N, 6.49; Cl, 24.63 Found C, 55.11; H, 5.64; N, 6.39; Cl, 24.14.

Example 2

1-(5,6-dichloro-3-oxoindan-1-carbonyl)-(2S)-2-(pyrrolidin-1-ylmethyl)piperidine hydrochloride 15 ml of methylene chloride solution containing 3.13 g (11.86 m mol) of 5,6-dichloro-3-oxoindan-1-carbonyl chloride was added dropwise at −10° C. to 15 ml of methylene chloride solution containing 1 g (5.94 m mol) of (2S)-2-(pyrrolidin-1-ylmethyl)piperidine and 1.82 ml (13.07 m mol) of triethylamine. After the addition, the reaction mixture was stirred at −10° C. for 1 hour, poured into ice water and extracted with methylene chloride. The methylene chloride extract was washed with saturated aqueous sodium chloride solution and dried over anhydrous sodium sulfate. After evaporation of the solvent, a mixture of two optically active isomers was obtained. Medium pressure liquid chromatography of the mixture using a mixed solvent of ethyl acetate and triethylamine (100:1) gave 0.65 g (27.7%) of one of the optically active isomers, $E_1$, eluted earlier, and 1.0 g (42.6%) of the other optically active isomer, $E_2$, eluted later.

Isomer $E_1$ was dissolved in acetone and mixed with a 4N 1,4-dioxane solution of hydrogen chloride. After evaporation down, the residue was recrystallized from a mixed solvent of methanol, acetone and diethyl ether to afford colorless prisms melting at 243°–244° C. (dec), and showing $[\alpha]_D+36°$ (c=0.5, methanol).

In a similar way, Isomer $E_2$ in the form of the hydrochloride was obtained as colorless needles melting at 194°–196° C. (dec), and showing $[\alpha]_D-56°$ (c=0.5, methanol).

Isomer $E_1$ is 1-[(1S)-5,6-dichloro-3-oxoindan-1-carbonyl]-(2S)-2-(pyrrolidin-1-ylmethyl)piperidine, and isomer $E_2$ is 1-[(1R)-5,6-dichloro-3-oxoindan-1-carbonyl]-(2S)-2-(pyrrolidin-1-ylmethyl)piperidine.

Isomer $E_1$ hydrochloride

Elemental analysis (%) $C_{20}H_{25}Cl_3N_2O_2$ Calcd C, 55.63; H, 5.84; N, 6.49; Cl, 24.63 Found C, 55.77; H, 5.88; N, 6.49; Cl, 24.65

Isomer $E_2$ hydrochloride

Elemental analysis (%) $C_{20}H_{25}Cl_3N_2O_2$ Calcd C, 55.63; H, 5.84; N, 6.49; Cl, 24.63 Found C, 55.31; H, 5.87; N, 6.48; Cl, 22.38.

Example 3

1-(5,6-dichloro-3-oxoindan-1-carbonyl)-(2R)-2-(pyrrolidin-1-ylmethyl)piperidine hydrochloride By following a procedure similar to that in Example 2, two optical isomers were obtained as their hydrochlorides from 1.25 g of (2R)-2-(pyrrolidin-1-yl-methyl)piperidine, 1.5 g of triethylamine and 1.96 g of 5,6-dichloro-3-oxoindan-1-carbonyl chloride. The products comprised 0.45 g of the hydrochloride of one of the optically active isomers ($E_1$), melting at 248°–250° C. (dec), and showing $[\alpha]_D-37°$ (c=0.5, methanol), and 0.38 g of the hydrochloride of the other isomer ($E_2$), melting at 199°–201° C. (dec), and showing $[\alpha]_D+58°$ (c=0.5, methanol).

Isomer $E_1$ is 1-[(1R)-5,6-dichloro-3-oxoindan-1-carbonyl]-(2R)-2-(pyrrolidin-1-ylmethyl)piperidine, and isomer $E_2$ is 1-[(1S)-5,6-dichloro-3-oxoindan-1-carbonyl]-(2R)-2-(pyrrolidin-1-ylmethyl)piperidine.

Isomer $E_1$ hydrochloride

Elemental analysis (%) $C_{20}H_{25}Cl_3N_2O_2$ Calcd C, 55.63; H, 5.84; N, 6.49; Cl, 24.63 Found C, 55.60; H, 5.78; N, 6.31; Cl, 24.49

Isomer $E_2$ hydrochloride

Elemental analysis (%) $C_{20}H_{25}Cl_3N_2O_2$ Calcd C, 55.63; H, 5.84; N, 6.49; Cl, 24.63 Found C, 55.33; H, 5.90; N, 6.38; Cl, 24.55.

Example 4

1-[(1S*)-5,6-dichloro-3-oxoindan-1-carbonyl]-(2S*)-2-(pyrrolidin-1-ylmethyl)piperidine hydrochloride and 1-[(1R*)-5,6-dichloro-3-oxoindan-1-carbonyl]-(2S*)-2-(pyrrolidin-1-ylmethyl)piperidine hydrochloride Using a procedure similar to that in Example 1, the title compounds were obtained from 5.0 g of 2-(pyrrolidin-1-ylmethyl)piperidine dihydrochloride, 5.3 g of 5,6-dichloro-3-oxoindan-1-carbonyl chloride and 80 ml of 1N aqueous sodium hydroxide solution. By medium pressure liquid chromatographic separation using a mixed solvent of ethyl acetate and triethylamine (100:1), 0.85 g of one of the diastereoisomers, $D_1$, eluted earlier, and 0.88 g of the other diastereoisomer, $D_2$, eluted later, were obtained. When each of these isomers was converted into its corresponding hydrochloride by treatment with a 4N 1,4-dioxane solution of hydrogen chloride, 0.97 g of the hydrochloride of isomer $D_1$, melting at 253°–255° C. (dec) and 0.83 g of the hydrochloride of the other isomer, $D_2$, melting at 228°–230° C. (dec) were obtained.

Diastereoisomer $D_1$ is 1-[(1S*)-5,6-dichloro-3-oxoindan-1-carbonyl]-(2S*)-2-(pyrrolidin-1-ylmethyl)piperidine and diastereoisomer $D_2$ is 1-[(1R*)-5,6-dichloro-3-oxoindan-1-carbonyl]-(2S*)-2-(pyrrolidin-1-ylmethyl)piperidine Diastereoisomer $D_1$ hydrochloride Elemental analysis (%) $C_{20}H_{25}Cl_3N_2O_2$ Calcd C, 55.63; H, 5.84; N, 6.49; Cl, 24.63 Found C, 55.48; H, 5.85; N, 6.47; Cl, 24.82

Diastereoisomer $D_2$ hydrochloride

Elemental analysis (%) $C_{20}H_{25}Cl_3N_2O_2$ Calcd C, 55.63; H, 5.84; N, 6.49; Cl, 24.63 Found C, 53.90; H, 6.00; N, 6.12; Cl, 24.83.

Example 5

1-(3-oxoindan-1-carbonyl)-2-(pyrrolidin-1-ylmethyl)piperidine hydrochloride

From 1.74 g of 2-(pyrrolidin-1-ylmethyl)piperidine, 2.21 g of 3-oxoindan-1-carbonyl chloride and 2.16 ml of triethylamine, 1.21 g of the title compound was obtained, melting at 190°–215° C. (dec), using a procedure similar to that in Example 2.

Elemental analysis (%) $C_{20}H_{27}ClN_2O_2$ Calcd C, 66.19; H, 7.50; N, 7.72; Cl, 9.77 Found C, 66.00; H, 7.62; N, 7.56; Cl, 9.56.

Example 6

1-(5-methyl-3-oxoindan-1-carbonyl)-2-(pyrrolidin-1-ylmethyl)piperidine hydrochloride From 2.7 g of 2-(pyrrolidin-1-ylmethyl)piperidine, 3.0 g of 5-methyl-3-oxoindan-1-carbonyl chloride and 2.0 g of triethylamine, 2.1 g of the title compound was obtained, melting at 153°–154° C. using a procedure similar to that in Example 2.

Elemental analysis (%) $C_{21}H_{29}ClN_2O_2$ Calcd C, 66.92; H, 7.76; N, 7.43; Cl, 9.41 Found C, 66.69; H, 7.80; N, 7.29; Cl, 9.23.

Example 7

1-(5-chloro-3-oxoindan-1-carbonyl)-2-(pyrrolidin-1-ylmethyl)piperidine hydrochloride To 100 ml of tetrahydrofuran solution containing 2.1 g of 5-chloro-3-oxoindan-1-carboxylic acid and 1.5 ml of triethylamine, 1.1 ml of ethyl chloroformate was added dropwise at −20° C. The reaction mixture was stirred for 20 minutes, 1.7 g of 2-(pyrrolidin-1-ylmethyl)piperidine was added, and the mixture was stirred for an additional 30 minutes. The reaction mixture was stirred further for 1 hour at room temperature. After completion of the reaction, the reaction mixture was poured into ice water and extracted with diethyl ether. The extract was washed with water, dried over anhydrous sodium sulfate, and the solvent was distilled off. The residue was subjected to silica gel column chromatography to obtain 0.8 g of the free amine of the title compound by elution with a mixed solvent of ethyl acetate and triethylamine (50:1). By treatment with a 4N 1,4-dioxane solution of hydrogen chloride, 0.6 g of the title compound was obtained, melting at 225°–230° C.

Elemental analysis (%) $C_{20}H_{26}Cl_2N_2O_2$ Calcd C, 60.46; H, 6.60; N, 7.05; Cl, 17.84 Found C, 60.19; H, 6.80; N, 6.99; Cl, 17.64.

Example 8

1-(6-methoxy-3-oxoindan-1-carbonyl)-2-(pyrrolidin-1-ylmethyl)piperidine hydrochloride From 1.21 g of 2-(pyrrolidin-1-ylmethyl)piperidine dihydrochloride, 1.35 g of 6-methoxy-3-oxoindan-1-carbonyl chloride and 2.79 ml of triethylamine, 0.72 g of the title compound was obtained, melting at 210°–228° C. (dec) using a procedure similar to that in Example 2.

Elemental analysis (%) $C_{21}H_{29}ClN_2O_3 \cdot 1/2 H_2O$ Calcd C, 62.75; H, 7.52; N, 6.97; Cl, 8.82 Found C, 62.51; H, 7.45; N, 6.83; Cl, 9.27.

Example 9

1-(4,5-dichloro-3-oxoindan-1-carbonyl)-2-(pyrrolidin-1-ylmethyl)piperidine hydrochloride From 1.18 g of 2-(pyrrolidin-1-ylmethyl)piperidine, 2.03 g of 4,5-dichloro-3-oxoindan-1-carbonyl chloride and 1.47 ml of triethylamine, 0.95 g of the title compound was obtained, melting at 148°–150° C. (dec) using a procedure similar to that in Example 2.

Elemental analysis (%) $C_{20}H_{25}Cl_3N_2O_2$ Calcd C, 55.63; H, 5.84; N, 6.49; Cl, 24.63 Found C, 55.11; H, 5.64; N, 6.39; Cl, 24.14.

Example 10

1-(6-hydroxy-3-oxoindan-1-carbonyl)-2-(pyrrolidin-1-ylmethyl)piperidine hydrochloride From 1.21 g of 2-(pyrrolidin-1-ylmethyl)piperidine dihydrochloride, 1.26 g of 6-hydroxy-3-oxoindan-1-carbonyl chloride and 2.8 ml of triethylamine, 0.1 g of the title compound was obtained, melting at 220°–231° C. (dec), using a procedure similar to that in Example 2.

Elemental analysis (%) $C_{20}H_{27}ClN_2O_3$ Calcd C, 63.40; H, 7.18; N, 7.39; Cl, 9.36 Found C, 63.60; H, 7.22; N, 7.84; Cl, 10.36.

Example 11

1-(5,6-dichloro-3-oxoindan-1-carbonyl)-2-(piperidinomethyl)piperidine hydrochloride From 1.5 g of 2-(piperidinomethyl)piperidine dihydrochloride, 2.5 g of 5,6-dichloro-3-oxoindan-1-carbonyl chloride and 45 ml of 1N aqueous sodium hydroxide solution, 1.1 g of the title compound was obtained, melting at 240°–245° C (dec), using a procedure similar to that in Example 1.

Elemental analysis (%) $C_{21} H_{27} Cl_3N_2O_3$ Calcd C, 54.62; H, 5.89; N, 6.07; Cl, 23.03 Found C, 54.60; H, 5.99; N, 6.00; Cl, 22.96.

Example 12

1-(1,2,3,4-tetrahydro-4-oxo-1-naphthoyl)-2-(pyrrolidin-1-ylmethyl)piperidine hydrochloride From 3.48 g of 2-(pyrrolidin-1-ylmethyl)piperidine dihydrochloride, 4.44 g of 1,2,3,4-tetrahydro-4-oxo-1-naphthoyl chloride and 63.9 ml of 1N aqueous sodium hydroxide solution, 4.17 g of the title compound was obtained, melting at 239°–242° C. (dec), using a procedure similar to that in Example 1.

Elemental analysis (%) $C_{21}H_{29}ClN_2O_2$ Calcd C, 66.92; H, 7.76; N, 7.43; Cl, 9.41 Found C, 66.34; H, 7.72; N, 7.24; Cl, 9.06.

Example 13

1-(6,7-dichloro-1,2,3,4-tetrahydro-4-oxo-1-naphthoyl)-2-(pyrrolidin-1-yl-methyl)piperidine hydrochloride From 0.89 g of 2-(pyrrolidin-1-ylmethyl)piperidine, 1.61 g of 6,7-dichloro-1,2,3,4-tetrahydro-4-oxo-1-naphthoyl chloride and 11 ml of triethylamine, 1.5 g of the title compound was obtained, melting at 255°–257° C. (dec), using a procedure similar to that in Example 2.

Elemental analysis (%) $C_{21}H_{27}Cl_3N_2O_2$ Calcd C, 56.58; H, 6.10; N, 6.28; Cl, 23.86 Found C, 55.86; H, 6.13; N, 6.16; Cl, 23.48.

Example 14

4,5-dihydro-6-oxo-4-[2-(pyrrolidin-1-ylmethyl) piperidine-1-carbonyl]-6H-cyclopenta[b]thiophene hydrochloride From 1.68 g of 2-(pyrrolidin-1-ylmethyl)piperidine, 2.2 g of 4,5-dihydro-6-oxo-6H-cyclopenta[b]thiophene-4- carbonyl chloride and 2.09 ml of triethylamine, 1.02 g of the title compound was obtained, melting at 189°–218° C. (dec), using a procedure similar to that in Example 2.

Elemental analysis (%) $C_{18}H_{25}ClN_2O_2S.1/2$ $H_2O$ Calcd C, 57.20; H, 6.68; N, 7.41; Cl, 9.38; S, 8.48 Found C, 56.91; H, 6.87; N, 7.13; Cl, 9.09; S, 8.25.

Example 15

1-(5-nitro-3-oxoindan-1-carbonyl)-2-(pyrrolidin-1-ylmethyl)piperidine hydrochloride From 1.21 g of 2-(pyrrolidin-1-ylmethyl)piperidine dihydrochloride, 1.32 g of 5-nitro-3-oxoindan-1-carbonyl chloride and 2.8 ml of triethylamine, 0.05 g of the title compound was obtained, melting at 154°–160° C. (dec), using a procedure similar to that in Example 2.

Elemental analysis (%) $C_{20}H_{26}ClN_3O_4$ Calcd C, 58.89; H, 6.43; N, 10.30; Cl, 8.69 Found C, 58.59; H, 6.29; N, 10.17; Cl, 8.48.

Example 16

1-(indan-1-carbonyl)-2-(pyrrolidin-1-ylmethyl)piperidine hydrochloride

From 2.36 g of 2-(pyrrolidin-1-ylmethyl)piperidine, 2.5 g of indene-1-carbonyl chloride and 4.88 ml of triethylamine, 1.4 g of 1-(indene-1-carbonyl)-2-(pyrrolidin-1-ylmethyl)piperidine was obtained using a procedure similar to that in Example 2. In a mixed solvent of methanol, water and ethanol (2:1:1), this compound was catalytically reduced with 10% palladium on carbon. After completion of the reduction, the catalyst was filtered off. After evaporation of the solvent, the residue was treated with a 4N 1,4-dioxane solution of hydrogen chloride to obtain 1.05 g of the title compound, melting at 218°–221° C.

Elemental analysis (%) $C_{20}H_{27}ClN_2O$ Calcd C, 69.25; H, 7.85; N, 8.08; Cl, 10.22 Found C, 69.26; H, 8.01; N, 7.60; Cl, 10.89.

Example 17

4-(3,4-dichlorophenylacetyl)-3-(pyrrolidin-1-ylmethyl)thiomorpholine hydrochloride 3-(Pyrrolidin-1-ylmethyl)thiomorpholine was generated from the corresponding hydrochloride, prepared as described in the Preparative Example which follows the Examples. A solution of 1.49 ml of triethylamine, and 1.0 g of 3-(pyrrolidin-1-ylmethyl)thiomorpholine dissolved in 50 ml of methylene chloride was cooled to 0° C. in an atmosphere of nitrogen with vigorous stirring. To the solution was added dropwise 5 ml of methylene chloride containing 1.44 g of 3,4-dichlorophenylacetyl chloride and the mixture was stirred at 3° C. for an hour and subsequently for 4 hours at room temperature.

After completion of the reaction, the reaction mixture was poured into a solution of sodium bicarbonate and extracted with ethyl acetate. The extract was washed with water and dried over anhydrous magnesium sulfate followed by concentration of the solvent by distillation under reduced pressure. The residue was purified by column chromatography through silica gel and 1.39 g of the desired compound was obtained from the fractions eluted with a 3:1 mixture of ethyl acetate and methanol. The product was dissolved in 20 ml of methylene chloride and mixed with a molar equivalent of a 4N 1,4-dioxane solution of hydrogen chloride. The mixture was concentrated and the residue was recrystallized from a mixture of ethanol and acetone to afford the title compound as colorless crystals, melting at 230°–239° C. (dec.).

Elemental analysis (%) $C_{17}H_{23}Cl_3N_2OS$ Calcd C, 49.83; H, 5.66; Cl, 25.95; N, 6.84; S, 7.82 Found C, 49.69; H, 5.69; Cl, 25.52; N, 6.53; S, 7.55.

Example 18

4-(3,4-dichlorophenylacetyl)-3-(pyrrolidin-1-ylmethyl)morpholine hydrochloride

The procedure described in Example 17 was repeated, but using 1.64 g of 3-(pyrrolidin-1-ylmethyl)morpholine, 3.72 ml of triethylamine and 1.54 g of 3,4-dichlorophenylacetyl chloride, to afford 0.72 g of the title compound, melting at 268° (dec.).

Elemental analysis (%) $C_{17}H_{23}Cl_3N_2O_2$ Calcd C, 51.86; H, 5.89; N, 7.11; Cl, 27.01 Found C, 51.68; H, 5.97; N, 7.20; Cl, 26.73.

Example 19

1-(3,4-dichlorophenylacetyl)-4-methyl-2-(pyrrolidin-1-ylmethyl)piperazine dihydrochloride The procedure described in Example 17, but using 1.0 g of 1-methyl-3-(pyrrolidin-1-ylmethyl)piperazine trihydrochloride, 2.1 ml of triethylamine and 0.8 g of 3,4-dichlorophenylacetyl chloride, to afford 1.01 g of the title compound, melting at 223°–227° C. (dec.).

Elemental analysis (%) $C_{18}H_{27}Cl_4N_3O.1/2$ $H_2O$ Calcd C, 47.80; H, 6.24; N, 9.29; Cl, 31.36 Found C, 47.63; H, 6.06; N, 9.40; Cl, 31.40.

Example 20

4-(4-methylphenylacetyl)-3-(pyrrolidin-1-ylmethyl)morpholine hydrochloride

To a solution of 1.33 g of 3-(pyrrolidin-1-ylmethyl)morpholine dihydrochloride in 30 ml of methylene chloride was added 1.5 ml of an aqueous solution containing 0.66 g of sodium hydroxide at 5° C. After the mixture was stirred vigorously, the organic layer was separated and dried over anhydrous magnesium sulfate. To a solution of 0.84 g of 4-methylphenylacetic acid, 0.78 ml of triethylamine and one drop of N-methylmorpholine in 30 ml of tetrahydrofuran was added a tetrahydrofuran solution containing 0.55 ml of ethyl chloroformate, followed by stirring at −20° to −15° C. for 20 minutes. To this stirred mixture was then added the previously prepared methylene chloride solution of 3-(pyrrolidin-1-ylmethyl)morpholine. The mixture was stirred at the same temperature for 30 minutes and subsequently for an hour at room temperature. After completion of the reaction, the reaction mixture was washed with a saturated aqueous solution of sodium chloride and dried over anhydrous magnesium sulfate. After distilling off the solvent, the residue was purified by column chromatography through silica gel and 0.56 g of the desired producted was obtained from the fraction eluted with a 3:1 mixture of ethyl acetate and methanol. The product was dissolved in methylene chloride and mixed with a molar equivalent of a 4N 1,4-dioxane solution of hydrogen chloride. The mixture was concentrated and recrystallized from a mixture of methanol and diethyl ether to afford the title compound, melting at 131° (dec.).

Elemental analysis (%) $C_{18}H_{27}ClN_2O_2.H_2O$ Calcd C, 60.58; H, 8.19; N, 7.85; Cl, 9.93 Found C, 61.16; H, 8.04; N, 7.78; Cl, 9.99.

Example 21

4-(4-methylthiophenylacetyl)-3-(pyrrolidin-1-ylmethyl)thiomorpholine hydrochloride The procedure described in Example 17 was repeated, but using 1.0 g of 3-(pyrrolidin-1-ylmethyl)thiomorpholine, 1.38 ml of triethylamine and 1.2 of 4-methylthiophenylacetyl chloride, to afford 1.36 g of the title compound, melting at 162°–166° C. (dec.).

Elemental analysis (%) $C_{18}H_{26}ClN_2OS_2$ Calcd C, 55.86; H, 7.03; N, 7.24; Cl, 9.16; S, 16.57 Found C, 55.48; H, 6.95; N, 6.96; Cl, 8.92; S, 16.83.

Example 22

3-(pyrrolidin-1-ylmethyl)-4-(2-thienylacetyl) thiomorpholine hydrochloride

The procedure described in Example 17 was repeated, but using 1.0 g of 3-(pyrrolidin-1-ylmethyl)thiomorpholine, 2.49 ml of triethylamine and 1.03 g of 2-thienylacetyl chloride, to afford 0.37 g of the title compound, melting at 204°–206° C. (dec.).

Elemental analysis (%) $C_{15}H_{23}ClN_2O_2$ Calcd C, 51.93; H, 6.68; N, 8.07; Cl, 10.22; S, 18.48 Found C, 51.85; H, 6.66; N, 8.10; Cl, 10.43; S, 18.24.

Example 23

3-(pyrrolidin-1-ylmethyl)-4-(2-thienylacetyl) morpholine hydrochloride

The procedure described in Example 17 was repeated, but using 0.88 g of 3-(pyrrolidin-1-ylmethyl)morpholine, 2.0 ml of triethylamine and 0.45 g of 2-thienylacetyl chloride, to afford 0.71 g of the title compound, melting at 215° C. (dec.).

Elemental analysis (%) $C_{15}H_{23}ClN_2O_2S$ Calcd C, 54.45; H, 7.01; N, 8.47; Cl, 10.71; S, 9.69 Found C, 54.44; H, 7.08; N, 8.58; Cl, 10.72; S, 9.61.

Example 24

1-(5,6-dichloro-3-oxoindan-1-carbonyl)-4-methyl-2-(pyrrolidin-1-ylmethyl)piperazine dihydrochloride To a suspension of 2.0 g of 4-methyl-2-(pyrrolidin-1-ylmethyl)piperazine trihydrochloride in 150 ml of methylene chloride was added 4.3 ml of triethylamine with vigorous stirring in an atmosphere of nitrogen. After stirring for 20 minutes, the mixture was cooled to −10° C. in an ice and salt bath and 50 ml of methylene chloride solution containing 1.9 g of 5,6-dichloro-3-oxoindan-1-carbonyl chloride was added dropwise to it. The reaction mixture was stirred at −10° C. for an hour and a half and subsequently at room temperature for two hours and a half and poured into a saturated aqueous solution of sodium bicarbonate. The resulting aqueous mixture was extracted with diethyl ether and the extract was washed with a saturated aqueous solution of sodium chloride followed by drying over anhydrous magnesium sulfate and distilling off the solvent. The residue was purified by column chromatography through silica gel and 1.60 g of the desired compound was obtained from the fractions eluted with a 10:3 mixture of ethyl acetate and triethylamine. To a solution of the product dissolved in methylene chloride was added a two molar quantity of a 4N 1,4-dioxane solution of hydrogen chloride and the mixture was concentrated. The residue was recrystallized from a mixture of ethanol and acetone to afford the title compound, melting at 250°–255° C. (dec.).

Elemental analysis (%) $C_{20}H_{27}Cl_4N_3O_2 \cdot 1/2\ H_2O$ Calcd C, 48.80; H, 5.73; N, 8.54; Cl, 28.81 Found C, 49.20; H, 5.73; N, 8.54; Cl, 29.05.

Example 25

4-methyl-1-(5-methyl-3-oxoindan-1-carbonyl)-2-(pyrrolidin-1-ylmethyl)piperazine dihydrochloride The procedure described in Example 24 was repeated, but using 1.0 g of 1-methyl-3-(pyrrolidin-1-ylmethyl)piperazine trihydrochloride, 2.1 ml of triethylamine and 0.75 g of 5-methyl-3-oxoindan-1-carbonyl chloride, to afford 0.84 g of the title compound, melting at 220°–223° C. (dec.).

Elemental analysis (%) $C_{21}H_{31}Cl_2N_3O_2 \cdot 1/2\ H_2O$ Calcd C, 57.66; H, 7.37; N, 9.61; Cl, 16.21 Found C, 57.86; H, 7.42; N, 9.32; Cl, 16.07.

Example 26

4-methyl-1-(3-oxoindan-1-carbonyl)-2-(pyrrolidin-1-ylmethyl)piperazine dihydrochloride The procedure described in Example 24 was repeated, but using 3.21 g of 1-methyl-3-(pyrrolidin-1-ylmethyl) piperazine trihydrochloride, 6.9 ml of triethylamine and 4.5 g of 3-oxoindan-1-carbonyl chloride, to afford 1.45 g of the title compound, melting at 252°–255° C. (dec.).

Elemental analysis (%) $C_{20}H_{29}Cl_2N_3O_2 \cdot 1/2\ H_2O$ Calcd C, 56.74; H, 7.14; N, 9.92; Cl, 16.75 Found C, 56.57; H, 7.25; N, 9.69; Cl, 16.56.

Example 27

1-(5,6-dichloroindan-1-carbonyl)-4-methyl-2-(pyrrolidin-1-ylmethyl)piperazine dihydrochloride The procedure described in Example 24 was repeated, but using 1.67 g of 1-methyl-3-(pyrrolidin-1-ylmethyl) piperazine trihydrochloride, 3.6 ml of triethylamine and 1.5 g of 5,6-dichloroindan-1-carbonyl chloride, to afford 1.54 g of the title compound, melting at 245°–250° C.

Elemental analysis (%) $C_{20}H_{29}Cl_4N_3O \cdot 1/2\ H_2O$ Calcd C, 50.23; H, 6.32; N, 8.79; Cl, 29.65 Found C, 50.09; H, 6.23; N, 8.74; Cl, 29.56.

Example 28

1-(6,7-dichloro-1,2,3,4-tetrahydro-4-oxo-1-naphthoyl)-4-methyl-2-(pyrrolidin-1-ylmethyl) piperazine dihydrochloride The procedure described in Example 24 was repeated, but using 1.0 g of 1-methyl-3-(pyrrolidin-1-ylmethyl)piperazine trihydrochloride, 2.1 ml of triethylamine and 1.0 g of 6,7-dichloro-1,2,3,4-tetrahydro-4-oxo-1-naphthoyl chloride, to afford 0.97 g of the title compound, melting at 275°–278° C. (dec.).

Elemental analysis (%) $C_{21}H_{29}Cl_4N_3O_2 \cdot 1/2\ H_2O$ Calcd C, 49.82; H, 5.97; N, 8.30; Cl, 28.01 Found C, 50.12; H, 5.83; N, 8.32; Cl, 27.90.

Example 29

1-(6-chloro-1,2,3,4-tetrahydro-4-oxo-1-naphthoyl)-4-methyl-2-(pyrrolidin-1-ylmethyl)piperazine dihydrochloride The procedure described in Example 24 was repeated, but using 1.0 g of 1-methyl-3-(pyrrolidin-1-ylmethyl)piperazine trihydrochloride, 2.1 ml of triethylamine and 0.87 g of 6-chloro-1,2,3,4-tetrahydro-4-oxo-1-naphthoyl chloride, to afford 0.92 g of the title compound, melting at 268°–274° C. (dec.).

Elemental analysis (%) $C_{21}H_{30}Cl_3N_3O_2$ Calcd C, 54.50; H, 6.53; N, 9.08; Cl, 22.98 Found C, 54.68; H, 6.36; N, 9.01; Cl, 22.64.

Example 30

4-(5,6-dichloro-3-oxoindan-1-carbonyl)-3-(pyrrolidin-1-ylmethyl)morpholine hydrochloride The procedure described in Example 24 was repeated, but using 0.88 g of 3-(pyrrolidin-1-ylmethyl)morpholine, 2.0 ml of triethylamine and 1.0 g of 5,6-dichloro-3-oxoindan-1-carbonyl chloride, to afford 0.66 g of the title compound, melting at 250°–257° C. (dec.).

Elemental analysis (%) $C_{19}H_{23}Cl_3N_2O_3 \cdot H_2O$ Calcd C, 50.51; H, 5.58; N, 6.20; Cl, 23.50 Found C, 50.43; H, 5.58; N, 6.27; Cl, 23.72.

Example 31

4-(3-oxoindan-1-carbonyl)-3-(pyrrolidin-1-ylmethyl)morpholine hydrochloride

The procedure described in Example 24 was repeated, but using 0.86 g of 3-(pyrrolidin-1-ylmethyl)morpholine, 1.96 ml of triethylamine and 0.89 g of 3-oxoindan-1-carbonyl chloride, to afford 0.35 g of the title compound, melting at 260°–265° C. (dec.).

Elemental analysis (%) $C_{19}H_{25}ClN_2O_3$ Calcd C, 62.54; H, 6.91; N, 7.68; Cl, 9.72 Found C, 62.26; H, 7.02; N, 7.73; Cl, 9.75.

Example 32

4-(5-methyl-3-oxoindan-1-carbonyl)-3-(pyrrolidin-1-ylmethyl)morpholine hydrochloride The procedure described in Example 24 was repeated, but using 0.89 g of 3-(pyrrolidin-1-ylmethyl)morpholine, 2.2 ml of triethylamine and 0.83 g of 5-methyl-3-oxoindan-1-carbonyl chloride, to afford 0.23 g of the title compound, melting at 225°–230° C.

Elemental analysis (%) $C_{20}H_{27}ClN_2O_3$ Calcd C, 63.40; H, 7.18; N, 7.39; Cl, 9.36 Found C, 63.50; H, 7.09; N, 7.40; Cl, 9.49.

Example 33

4-(5-chloro-3-oxoindan-1-carbonyl)-3-(pyrrolidin-1-ylmethyl)morpholine hydrochloride The procedure described in Example 24 was repeated, but using 0.89 g of 3-(pyrrolidin-1-ylmethyl)morpholine, 2.0 ml of triethylamine and 0.91 g of 5-chloro-3-oxoindan-1-carbonyl chloride, to afford 0.83 g of the title compound, melting at 220°–229° C. (dec.).

Elemental analysis (%) $C_{19}H_{24}Cl_2N_2O_3$ Calcd C, 57.15; H, 6.06; N, 7.02; Cl, 17.76 Found C, 56.90; H, 6.01; N, 7.00; Cl, 17.55.

Example 34

4-(5,6-dichloro-3-oxoindan-1-carbonyl)-3-(morpholinomethyl)morpholine hydrochloride The procedure described in Example 24 was repeated, but using 1.25 g of 3-(morpholinomethyl)morpholine, 2.67 ml of triethylamine and 1.11 g of 5,6-dichloro-3-oxoindan-1-carbonyl chloride, to afford 0.7 g of the title compound, melting at 210°–216° C. (dec.).

Elemental analysis (%) $C_{19}H_{23}Cl_3N_2O_4$ Calcd C, 50.74; H, 5.15; N, 6.23; Cl, 23.65 Found C, 50.43; H, 5.04; N, 6.16; Cl, 23.40.

Example 35

4-(5-chloro-3-oxoindan-1-carbonyl)-3-(dimethylaminomethyl)morpholine hydrochloride The procedure described in Example 24 was repeated, but using 0.90 g of 3-dimethylaminomethylmorpholine, 2.3 ml of triethylamine and 1.03 g of 5-chloro-3-oxoindan-1-carbonyl chloride, to afford 1.03 g of the title compound, melting at 230°–240° C.

Elemental analysis (%) $C_{17}H_{22}Cl_2N_2O_3$ Calcd C, 54.70; H, 5.94; N, 7.50; Cl, 19.00 Found C, 54.36; H, 6.28; N, 7.28; Cl, 19.21.

Example 36

4-(5,6-dichloro-3-oxoindan-1-carbonyl)-3-(pyrrolidin-1-ylmethyl)thiomorpholine hydrochloride The procedure described in Example 24 was repeated, but using 0.6 g of 3-(pyrrolidin-1-ylmethyl)thiomorpholine, 0.6 g of triethylamine and 1.0 g of 5,6-dichloro-3-oxoindan-1-carbonyl chloride, to afford 0.39 g of the title compound, melting at 215°–223° C.

Elemental analysis (%) $C_{19}H_{23}Cl_3N_2O_2S \cdot H_2O$ Calcd C, 48.74; H, 5.34; N, 5.99; S, 6.85 Found C, 48.46; H, 5.34; N, 5.90; S, 7.02.

Example 37

4-(5-methyl-3-oxoindan-1-carbonyl)-3-(pyrrolidin-1-ylmethyl)thiomorpholine hydrochloride The procedure described in Example 24 was repeated, but using 0.92 g of 3-(pyrrolidin-1-ylmethyl)thiomorpholine, 1.64 ml of triethylamine and 1.66 g of 5-methyl-3-oxoindan-1-carbonyl chloride, to afford 1.35 g of the title compound, melting at 232°–234° C.

Elemental analysis (%) $C_{20}H_{27}ClN_2O_2S$ Calcd C, 60.82; H, 6.89; N, 7.09; Cl, 8.97; S, 8.11 Found C, 60.57; H, 6.77; N, 7.06; Cl, 8.69; S, 8.38

Example 38

4-(5-chloro-3-oxoindan-1-carbonyl)-3-(pyrrolidin-1-ylmethyl)thiomorpholine hydrochloride The procedure described in Example 24 was repeated, but using 3.7 g of 3-(pyrrolidin-1-ylmethyl)thiomorpholine, 3.42 ml of triethylamine and 4.56 g of 5-chloro-3-oxoindan-1-carbonyl chloride, to afford 2.8 g of the title compound, melting at 200°–205° C. (dec.).

Elemental analysis (%) $C_{19}H_{24}Cl_2N_2O_2S$ Calcd C, 54.94; H, 5.82; N, 6.74; Cl, 17.07; S, 7.72 Found C, 54.99; H, 6.02; N, 6.65; Cl, 16.82; S, 7.63.

Example 39

4-(6-methoxy-3-oxoindan-1-carbonyl)-3-(pyrrolidin-1-ylmethyl)thiomorpholine hydrochloride The procedure described in Example 24 was repeated, but using 0.97 g of 3-(pyrrolidin-1-ylmethyl)thiomorpholine, 1.39 ml of triethylamine and 1.23 g of 6-methoxy-3-oxoindan-1-carbonyl chloride, to afford 0.9 g of the title compound, melting at 225°–233° C.

Elemental analysis (%) $C_{20}H_{27}ClN_2O_3S$ Calcd C, 58.45; H, 6.62; N, 6.82; Cl, 8.63; S, 7.80 Found C, 58.55; H, 6.85; N, 6.59; Cl, 8.50; S, 7.62.

Example 40

4,5-dihydro-6-oxo-4-[3-(pyrrolidin-1-ylmethyl)thiomorpholine-1-carbonyl]-6H-cyclopenta[b]thiophene hydrochloride The procedure described in Example 24 was repeated, but using 0.96 g of 3-(pyrrolidin-1-ylmethyl)thiomorpholine, 1.39 ml of triethylamine and 1.0 g of 4,5-dihydro-6-oxo-6H-cyclopenta[b]thiophene-4-carbonyl chloride, to afford 0.5 g of the title compound, melting at 204°–223° C.

Elemental analysis (%) $C_{17}H_{23}ClN_2O_2S_2 \cdot 1/2\ H_2O$ Calcd C, 51.57; H, 6.11; N, 7.07; Cl, 8.95; S, 16.19 Found C, 51.71; H, 6.09; N, 7.08; Cl, 8.76; S, 16.30.

Example 41

4-[(1S*)-5,6-dichloroindan-1-carbonyl]-(3S*)-3-(pyrrolidin-1-ylmethyl)thiomorpholine hydrochloride, and 4-[(1R*)-5,6-dichloroindan-1-carbonyl]-(3S*)-3-(pyrrolidin-1-ylmethyl)thiomorpholine hydrochloride The procedure described in Example 24 was repeated, but using 0.72 g of 3-(pyrrolidin-1-ylmethyl)thiomorpholine, 0.8 ml of triethylamine and 1.08 g of 5,6-dichloroindan-1-carbonyl chloride, to afford the title compounds as diastereoisomers, which were separated by column chromatography under medium pressure using a mixed solvent of ethyl acetate and triethylamine (100:1). There were obtained 0.57 g of diastereoisomer $D_1$ in the earlier effluent and 0.19 g of diastereoisomer $D_2$ in the later effluent. Each diastereoisomer was converted to diastereoisomer $D_1$ hydrochloride, melting at 220°–230° C. and diastereoisomer $D_2$ hydrochloride, melting at 230°–242° C., respectively.

Diastereoisomer $D_1$ is 4-[(1S*)-5,6-dichloroindan-1-carbonyl]-(3S*)-3-(pyrrolidin-1-ylmethyl)thiomorpholine, and diastereoisomer $D_2$ is 4-[(1R*)-5,6-dichloroindan-1-carbonyl]-(3S*)-3-(pyrrolidin-1-ylmethyl)thiomorpholine
Diastereoisomer $D_1$ hydrochloride Elemental analysis (%) $C_{19}H_{25}Cl_3N_2OS$ Calcd C, 52.36; H, 5.78; N, 6.43; Cl, 24.40; S, 7.36 Found C, 52.25; H, 5.70; N, 6.50; Cl, 24.61; S, 7.35
Diastereoisomer $D_2$ hydrochloride Elemental analysis (%) $C_{19}H_{25}Cl_3N_2OS$ Calcd C, 52.36; H, 5.78; N, 6.43; Cl, 24.40; S, 7.36 Found C, 52.28; H, 5.70; N, 6.60; Cl, 24.52; S, 7.29.

Example 42

4-(5,6-dichloro-3-oxoindan-1-carbonyl)-3-(piperidinomethyl)thiomorpholine hydrochloride The procedure described in Example 24 was repeated, but using 0.9 g of 3-(piperidinomethyl)thiomorpholine, 1.0 g of triethylamine and 1.5 g of 5,6-dichloro-3-oxoindan-1-carbonyl chloride, to afford 0.45 g of the title compound, melting at 146°–155° C.

Elemental analysis (%) $C_{20}H_{25}Cl_3N_2O_2S \cdot H_2O$ Calcd C, 49.80; H, 5.60; N, 5.81; Cl, 22.07; S, 6.65 Found C, 49.54; H, 5.57; N, 5.81; Cl, 22.35; S, 6.70.

Example 43

4-[(1S*)-6,7-dichloro-1,2,3,4-tetrahydro-4-oxo-1-naphthoyl]-(3S*)-3-(pyrrolidin-1-ylmethyl)thiomorpholine hydrochloride, and 4-[(1R*)-6,7-dichloro-1,2,3,4-tetrahydro-4-oxo-1-naphthoyl]-(3S*)-3-(pyrrolidin-1-ylmethyl)thiomorpholine hydrochloride According to a manner similar to that of Example 24, the reaction products prepared from 3.7 g of 3-(pyrrolidin-1-ylmethyl)thiomorpholine, 3.4 ml of triethylamine and 5.5 g of 6,7-dichloro-1,2,3,4-tetrahydro-4-oxo-1-naphthoyl chloride were separated by column chromatography under medium pressure using a mixed solvent of ethyl acetate and triethylamine (100:1). Diastereoisomer $D_1$ (1.9 g) was obtained from the fractions eluted earlier and diastereoisomer $D_2$ (2.8 g) from the fractions eluted later. Each isomer was converted into diastereoisomer $D_1$ hydrochloride, melting at 263°–264° C. and diastereoisomer $D_2$ hydrochloride, melting at 264°–265° C. respectively.

Diastereoisomer $D_1$ is 4-[(1S*)-6,7-dichloro-1,2,3,4-tetrahydro-4-oxo-1-naphthoyl]-(3S*)-3-(pyrrolidin-1-ylmethyl)thiomorpholine hydrochloride, and diastereoisomer $D_2$ is 4-[(1R*)-6,7-dichloro-1,2,3,4-tetrahydro-4-oxo-1-naphthoyl]-(3S*)-3-(pyrrolidin-1-ylmethyl)thiomorpholine hydrochloride
Diastereoisomer $D_1$ hydrochloride Elemental analysis (%) $C_{20}H_{25}N_2O_2Cl_3S$ Calcd C, 51.79; H, 5.43; N, 6.04; Cl, 22.93; S, 6.91 Found C, 51.57; H, 5.70; N, 5.90; Cl, 23.02; S, 6.85
Diastereoisomer $D_2$ hydrochloride Elemental analysis (%) $C_{20}H_{25}N_2O_2Cl_3S$ Calcd C, 51.79; H, 5.43; N, 6.04; Cl, 22.93; S, 6.91 Found C, 51.79; H, 5.69; N, 6.05; Cl, 22.86; S, 6.86.

Example 44

4-(6-chloro-1,2,3,4-tetrahydro-4-oxo-1-naphthoyl)-3-(pyrrolidin-1-ylmethyl)thiomorpholine hydrochloride The procedure described in Example 24 was repeated, but using 1.0 g of 3-(pyrrolidin-1-ylmethyl)thiomorpholine, 1.38 ml of triethylamine and 1.5 g of 6-chloro-1,2,3,4-tetrahydro-4-oxo-1-naphthoyl chloride, to afford 1.76 g of the title compound, melting at 195°–200° C.

Elemental analysis (%) $C_{20}H_{26}N_2O_2Cl_2S \cdot H_2O$ Calcd C, 53.69; H, 6.30; N, 6.26; Cl, 15.85; S, 7.17 Found C, 53.72; H, 6.04; N, 6.28; Cl, 15.58; S, 7.07.

4-(6,7-dichloro-1,2,3,4-tetrahydro-4-oxo-1-naphthoyl)-3-(piperidinomethyl)thiomorpholine hydrochloride The procedure described in Example 24 was repeated, but using 2.0 g of 3-(piperidinomethyl)thiomorpholine, 2.2 ml of triethylamine and 3.52 g of 6,7-dichloro-1,2,3,4-tetrahydro-4-oxo-1-naphthoyl chloride, to afford 3.67 g of the title compound, melting at 245°–254° C. (dec.).

Elemental analysis (%) $C_{21}H_{27}N_2O_2Cl_3S$ Calcd C, 52.78; H, 5.70; N, 5.86; Cl, 22.26; S, 6.71 Found C, 53.00; H, 6.01; N, 5.60; Cl, 21.93; S, 6.47.

Example 46

4-(5,6-dichloro-3-oxoindan-1-carbonyl)-(3R)-3-(pyrrolidin-1-ylmethyl)thiomorpholine A solution (15 ml) of 3.0 g of 5,6-dichloro-3-oxoindan-1-carboxylic acid chloride in methylene chloride was dropwise added at −10° C. to a 15 ml of methylene chloride solution of (3R)-3-(pyrrolidin-1-ylmethyl)thiomorpholine (1 g) and triethylamine (2 ml). The reaction mixture was stirred for 1 hour at −10° C. and poured into ice-water. The mixture was extracted with methylene chloride. Then, the extract was washed with a saturated solution of sodium chloride and dried over anhydrous sodium sulfate. The solvent was evaporated under reduced pressure to give a mixture of two optical isomers. This mixture was subjected to medium pressure liquid chromatography and eluted using a mixed solvent of ethyl acetate and triethylamine (100:1), to yield 0.8 g of an optical isomer $E_1$ (oil) as a first fraction and 1.0 g of an optical isomer $E_2$ (oil) as a second fraction. Isomer $E_1$ is the (1S) isomer, and isomer $E_2$ is the (1R) isomer.

Example 47

1-(5,6-dichloroindan-1-carbonyl)-2-(pyrrolidin-1-ylmethyl)piperidine hydrochloride From 1.18 g of 2-(pyrrolidin-1-ylmethyl)piperidine, and 1.87 g of 5,6-dichloroindan-1-carbonyl chloride, 0.51 g of the title compound was obtained, melting at 245°–250° C., using a procedure similar to that in Example 1.

Elemental analysis (%) $C_{20}H_{27}Cl_3N_2O$ Calcd C, 57.50; H, 6.51; N, 6.70; Cl, 25.46 Found C, 57.25; H, 6.58; N, 6.62; Cl, 25.25.

Example 48

1-(5,6-dichloro-3-oxoindan-1-carbonyl)-2-(morpholinomethyl)piperidine hydrochloride From 0.93 g of 2-(morpholinomethyl)piperidine, and 1.00 g of 5,6-dichloro-3-oxoindan-1-carbonyl chloride, 0.85 g of the title compound was obtained, melting at 235°–240° C. using a procedure similar to that in Example 1.

Elemental analysis (%) $C_{20}H_{25}Cl_3N_2O_3$ Calcd C, 53.65; H, 5.63; N, 6.26; Cl, 23.75 Found C, 53.47; H, 5.72; N, 6.31; Cl, 23.57.

Example 49

4-[2-(3,4-dichlorophenyl)propionyl]-3-(pyrrolidin-1-ylmethyl)thiomorpholine hydrochloride From 1.86 g of 3-(pyrrolidin-1-ylmethyl)thiomorpholine, and 2.4 g of 2-(3,4-dichlorophenyl)propionyl chloride, 0.71 g of the title compound was obtained, melting at 224°–230° C. using a procedure similar to that in Example 1.

Elemental analysis (%) $C_{18}H_{25}Cl_3N_2OS$ Calcd C, 51.00; H, 5.90; N, 6.61; Cl, 25.15; S, 7.56 Found C, 51.18; H, 6.05; N, 6.60; Cl, 25.57; S, 7.22.

Pharmaceutical Example
Capsule

The compound of Example 36 (1 mg) was triturated in to a 1:50 compound with lactose, and the resulting powder was again triturated in to a 1:20 powder with lactose, giving Powder A.

100 mg of Powder A and 0.5 mg of magnesium stearate were packed in to capsules (No. 5).

Preparative Example 3-(pyrrolidin-1-ylmethyl)thiomorpholine dihydrochloride (a) 4-(t-butoxycarbonyl)thiomorpholine-3-carboxylic acid Triethylamine (23.6 ml) was added at 0° C. to a solution of DL-thiomorpholine-3-carboxylic acid (5 g) in 40 ml of a 1:1 mixture of 1,4-dioxane and water. Thereafter, di-t-butyl dicarbonate (8.16 g) was added and the reaction mixture was stirred for 30 minutes at 0° C. and for 3 hours at room temperature. The solvent was evaporated under reduced pressure and the residue was dissolved in 100 ml of ethyl acetate. The pH of the reaction solution was adjusted to 4 using saturated citric acid solution and extracted with ethyl acetate. The organic layer was dried over anhydrous sodium sulfate and concentrated under reduced pressure. The residue was recrystallized from hexane/ethyl acetate to yield 6.0 g (71%) of 4-(t-butoxycarbonyl)thiomorpholine-3-carboxylic acid.

(b) 3-(pyrrolidine-1-carbonyl)thiomorpholine

Triethylamine (3.1 ml), followed by a solution of pyrrolidine (2.0 ml) in 10 ml of tetrahydrofuran, was added at 0° C. under a stream of nitrogen to a solution of 5.0 g of 4-(t-butoxycarbonyl)thiomorpholine-3-carboxylic acid in 100 ml of tetrahydrofuran. After the mixture had been stirred for 1 hour, a solution of 3.6 g of ethyl cyanophosphate in 10 ml of tetrahydrofuran was added to the mixture and the mixture was stirred for 5 hours. Water was added to the reaction mixture and the mixture was extracted with ethyl acetate. The organic layer was dried over anhydrous magnesium sulfate and the solvent was concentrated under reduced pressure. The residue was recrystallized from ethyl acetate/hexane to yield 4.61 g (74%) of 4-(t-butoxycarbonyl)-3-(pyrrolidine-1-carbonyl)thiomorpholine.

4-(t-butoxycarbonyl)-3-(pyrrolidine-1-carbonyl)thiomorpholine (3.2 g) was dissolved in 50 ml of methanol. A 4N 1,4-dioxane solution of hydrogen chloride (13.1 ml) was added, and the solution was condensed to yield white crystals. These crystals was recrystallized from ethanol and diethyl ether to give 2.47 g (96%) of 3-(pyrrolidine-1-carbonyl)thiomorpholine monohydrochloride.

A 1N aqueous sodium hydroxide solution (12.5 ml) was added to a mixture of 2.47 g of 3-(pyrrolidine-1-carbonyl)thiomorpholine monohydrochloride and 20 ml of methylene chloride. The organic layer was extracted and dried over anhydrous magnesium sulfate. The solvent was evaporated under reduced pressure to yield 1.75 g (83%) of 3-(pyrrolidine-1-carbonyl)thiomorpholine (c) 3-(pyrrolidin-1-ylmethyl)thiomorpholine dihydrochloride A solution of 1.6 g of 3-(pyrrolidine-1-carbonyl) thiomorpholine in 200 ml of tetrahydrofuran was added dropwise to a mixture of 1.0 g of lithium aluminum hydride and 100 ml of tetrahydrofuran under ice-cooling and a stream of nitrogen. Excess lithium aluminum hydride was decomposed using 15 g of sodium sulfate decahydrate. Celite filtration using methylene chloride was carried out. The solvent was concentrated under reduced pressure to yield 1.37 g (93%) of 3-(pyrrolidin-1-ylmethyl) thiomorpholine.

A mixture of 260 mg of 3-(pyrrolidin-1-ylmethyl) thiomorpholine and 5 ml of 1,4-dioxane was treated with 150 µl of 4N 1,4-dioxane solution of hydrogen chloride. The solvent was evaporated under reduced pressure to yield 354 mg (98%) of 3-(pyrrolidin-1-ylmethyl)thiomorpholine dihydrochloride, melting at 218°–220° C.

Elemental Analysis (%) $C_9H_{20}N_2SCl_2$ Calcd C, 41.70; H, 7.78; N, 10.80; S, 12.37; Cl, 27.35 Found C, 41.57; H, 8.04; N, 10.61; S, 12.25; Cl, 27.30.

We claim:

1. A process for preparing a compound of the formula (I):

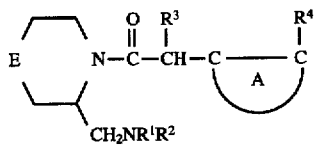

in which,

R$^1$ and R$^2$ are the same or different and each of R$^1$ and R$^2$ is selected from the group consisting of a hydrogen atom and a C$_1$–C$_6$ alkyl group, or R$^1$ and R$^2$ together with the nitrogen atom to which they are attached to form a 5-membered or 6-membered N-heterocyclic ring which optionally has a further heteroatom selected from the group consisting of oxygen, nitrogen and sulfur;

E is a methylene group;

ring A is selected from the group consisting of an unsubstituted aryl ring selected from the group consisting of benzene and naphthalene; and an aryl ring substituted with at least one substituent selected from the group consisting of a halogen atom, a C$_1$–C$_6$ alkyl group, a halogenated C$_1$–C$_6$ alkyl group, a C$_1$–C$_6$ alkoxy group, a halogenated C$_1$–C$_6$ alkoxy group, a C$_1$–C$_6$ alkylthio group, an aryl group selected from the group consisting of phenyl and naphthyl, an aliphatic acyl group having 1 to 6 carbon atoms selected from the group consisting of formyl, acetyl, propionyl, butyryl, isobutyryl, valeryl, isovaleryl, pivaloyl and hexanoyl, a nitro group and a hydroxy group;

R$^3$ and R$^4$ together are a group of formula (IV)

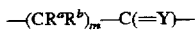

wherein each of R$^a$ and R$^b$ is a hydrogen atom or a C$_1$–C$_3$ alkyl group, provided that there are not more than three alkyl groups in the group of formula (IV), m is 1, 2, or 3, and Y is two hydrogen atoms or an oxygen atom;

or a pharmaceutically acceptable salt thereof;

which process comprises reacting an acid of formula (II)

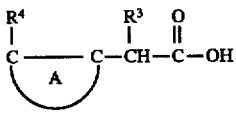

wherein R$^3$, R$^4$, and ring A are as defined above, with an amine of formula (III)

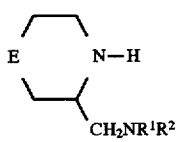

wherein R$^1$, R$^2$ and E are as defined above.

2. The process of claim 1, which further comprises carrying out the process in the presence of a base in an inert solvent.

3. The process of claim 2, wherein the base is selected from the group consisting of triethylamine, sodium carbonate, potassium carbonate, sodium hydroxide and potassium hydroxide.

4. The process of claim 3, wherein the inert solvent is an organic solvent selected from the group consisting of methylene chloride, chloroform, carbon tetrachloride, 1,2-dichloroethane, diethyl ether, tetrahydrofuran and 1,4-dioxane.

5. The process of claim 4, wherein the process is carried out at a temperature of −30° C. to the reflux temperature of the solvent.

6. The process of claim 5, wherein the temperature is −10° C. to room temperature.

7. The process of claim 3, wherein the inert solvent is water and the process is carried out at a temperature of −5° C. to 0° C.

8. The process of claim 6, which further comprises carrying out the process for 30 minutes to 3 hours.

9. The process of claim 7, which further comprises carrying out the process for 30 minutes to 3 hours.

10. A process for preparing a compound of the formula (I):

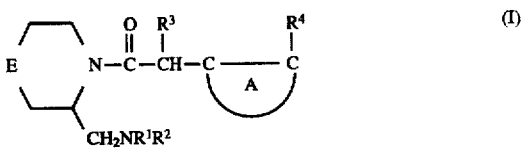

in which,

R$^1$ and R$^2$ are the same or different and each of R$^1$ and R$^2$ is selected from the group consisting of a hydrogen atom and a C$_1$–C$_6$ alkyl group, or R$^1$ and R$^2$ together with the nitrogen atom to which they are attached form a 5-membered or 6-membered N-heterocyclic ring which optionally has a further heteroatom selected from the group consisting of oxygen, nitrogen and sulfur;

E is a methylene group;

ring A is selected from the group consisting of an unsubstituted aryl ring selected from the group consisting of benzene and naphthalene; and an aryl ring substituted with at least one substituent selected from the group consisting of a halogen atom, a C$_1$–C$_6$ alkyl group, a halogenated C$_1$–C$_6$ alkyl group, a C$_1$–C$_6$ alkoxy group, a halogenated C$_1$–C$_6$ alkoxy group, a C$_1$–C$_6$ alkylthio group, an aryl group selected from the group consisting of phenyl and naphthyl, an aliphatic acyl group having 1 to 6 carbon atoms selected from the group consisting of formyl, acetyl, propionyl, butyryl, isobutyryl, valeryl, isovaleryl, pivaloyl and hexanoyl, a nitro group and a hydroxy group;

R$^3$ and R$^4$ together are a group of formula (IV)

wherein each of R$^a$ and R$^b$ is a hydrogen atom or a C$_1$–C$_3$ alkyl group, provided that there are not more than three alkyl groups in the group of formula (IV), m is 1, 2, or 3, and Y is two hydrogen atoms or an oxygen atom;

or a pharmaceutically acceptable salt thereof;

which process comprises reacting an acyl halide or a mixed acid anhydride of an acid of formula (II)

wherein R$^3$, R$^4$, and ring A are as defined above, with an amine of formula (III)

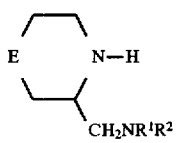

(III)

wherein $R^1$, $R^2$ and E are as defined above, or the acid of the formula (II) is reacted with the amine of the formula (III) in the presence of a condensing reagent, or the acid of the formula (II) is employed in the form of a compound which is an unsaturated acid which is reduced after the reaction with the amine of the formula (III).

11. The process of claim 10, wherein the acyl halide is selected from the group consisting of acyl chloride, acyl bromide and acyl iodide.

12. The process of claim 10, wherein the acid of the formula (II) is in a form of a mixed acid anhydride which is obtained by reacting the acid with a haloformate of the formula Hal-COOR$^5$, wherein $R^5$ is a $C_1$–$C_3$ alkyl, in the presence of an organic base in an inert solvent, at a temperature of –20° C. to the reflux temperature of the solvent for 30 minutes to 12 hours.

13. The process of claim 10, wherein the acid of the formula (II) is reacted with the amine of the formula (III) in the presence of a condensing agent selected from the group consisting of triphenylphosphine, 2,2'-pyridine disulfide and 1,3-dicyclohexylcarbodiimide, in a solvent selected from the group consisting of tetrahydrofuran, acetonitrile and dimethylformamide, at a temperature of –20° C. to 100° C. and for 30 minutes to 24 hours.

14. The process of claim 10, wherein $R^1$ and $R^2$ together with the nitrogen atom to which they are attached form a heterocyclic ring which is selected from the group consisting of imidazolidinyl, hexahydropyridazinyl, hexahydropyrimidinyl, piperazinyl, hexamethyleneimino, 1,2-diazacycloheptyl, 1,3-diazacycloheptyl, homopiperazinyl, pyrrolyl, azepinyl, thiazolidinyl, morpholinyl, thiomorpholinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl, pyrazinyl, quinolyl, isoquinolyl, acridyl, tetrahydroacridyl, pyrrolidinyl, piperidino, tetrahydroquinolyl, tetrahydroisoquinolyl, isoindolyl, indolinyl and 6-azabicyclo(3.2.1)oct-6-yl, said heterocyclic ring being unsubstituted or substituted by a straight or branched $C_1$–$C_6$ alkyl group.

15. The process of claim 1, wherein the compound of formula (I) is converted into a pharmaceutically acceptable acid addition salt.

* * * * *

UNITED STATES PATENT AND TRADEMARK OFFICE
CERTIFICATE OF CORRECTION

PATENT NO. : 5,756,730
DATED : May 26, 1998
INVENTOR(S) : TERADA et al

It is certified that error appears in the above-identified patent and that said Letters Patent is hereby corrected as shown below:

Column 36, line 6 (Claim 14): after "claim" delete "10" and insert --1--.

Signed and Sealed this

Ninth Day of May, 2000

Attest:

Attesting Officer

Q. TODD DICKINSON
Director of Patents and Trademarks